United States Patent
Arunachalam

(10) Patent No.: US 10,323,281 B2
(45) Date of Patent: Jun. 18, 2019

(54) KITS AND METHODS FOR EVALUATING, SELECTING AND CHARACTERIZING TISSUE CULTURE MODELS USING MICRO-RNA PROFILES

(71) Applicant: Padma Arunachalam, Arcadia, CA (US)

(72) Inventor: Padma Arunachalam, Arcadia, CA (US)

( * ) Notice: Subject to any disclaimer, the term of this patent is extended or adjusted under 35 U.S.C. 154(b) by 205 days.

(21) Appl. No.: 14/777,811

(22) PCT Filed: Mar. 20, 2014

(86) PCT No.: PCT/US2014/031362
§ 371 (c)(1),
(2) Date: Sep. 17, 2015

(87) PCT Pub. No.: WO2014/153471
PCT Pub. Date: Sep. 25, 2014

(65) Prior Publication Data
US 2016/0298189 A1    Oct. 13, 2016

Related U.S. Application Data

(60) Provisional application No. 61/857,903, filed on Jul. 24, 2013, provisional application No. 61/845,150, filed on Jul. 11, 2013, provisional application No. 61/803,579, filed on Mar. 20, 2013.

(51) Int. Cl.
| | |
|---|---|
| *C12Q 1/6881* | (2018.01) |
| *G16B 25/00* | (2019.01) |
| *G16B 40/00* | (2019.01) |
| *C12Q 1/68* | (2018.01) |
| *C12Q 1/6886* | (2018.01) |
| *C12Q 1/6809* | (2018.01) |

(52) U.S. Cl.
CPC ......... *C12Q 1/6881* (2013.01); *C12Q 1/6809* (2013.01); *C12Q 1/6886* (2013.01); *C12Q 2600/136* (2013.01); *C12Q 2600/158* (2013.01); *C12Q 2600/178* (2013.01); *G16B 25/00* (2019.02); *G16B 40/00* (2019.02)

(58) Field of Classification Search
None
See application file for complete search history.

(56) References Cited

U.S. PATENT DOCUMENTS

| | | |
|---|---|---|
| 6,998,264 B2 | 2/2006 | Ingram |
| 2012/0041683 A1 | 2/2012 | Vaske et al. |
| 2012/0259000 A1 | 10/2012 | Marionnet et al. |

FOREIGN PATENT DOCUMENTS

| | | |
|---|---|---|
| WO | 2009/108856 A2 | 9/2009 |
| WO | 2012/115885 A1 | 8/2012 |
| WO | 2012/138691 A2 | 10/2012 |

OTHER PUBLICATIONS

Guo et al (Biomed Res. Int 2014: Article ID 782490, 7 pages, 2014) (Year: 2014).*
Sharma et al (Nature Reviews 10: 241-253, 2010) (Year: 2010).*
Ling et al (Nature Reviews 12:847-865) (Year: 2013).*
Mitra et al (Trends in Biotechnology 2013, 31(6): 347-354) (Year: 2013).*
Mitra et al (Molecular Vision 2012; 18:1361-1378) (Year: 2012).*
Yeon et al (PLOS ONE 8(9): e73345, 12 pages) (Year: 2013).*
Piovan et al (Mol. Oncol. 6:458-472, 2012) (Year: 2012).*
Nam et al (BMC Medical Genomics 2012, 5:18) (Year: 2012).*
Debeb et al (Molecular Cancer 2010, 9:180) (Year: 2010).*
Tsunoda et al (Anticancer Research 31: 2453-2460 (2011) (Year: 2011).*
Supplementary European Search Report dated Oct. 12, 2016 for Application No. EP 14 77 1009.
Nguyen, H. T., et al., "The microRNA expression associated with morphogenesis of breast cancer cells in three-dimensional organotypic culture", Oncology Reports, vol. 28, Apr. 19, 2012, pp. 117-126.
Li, C., et al., "Comparative profiling of miRNA expression of lung adenocarcinoma cells in two-dimensional and three-dimensional cultures", Gene, vol. 511, No. 2, Dec. 1, 2012, pp. 143-150.
Ota, T, et al., "KRAS Up-regulates the Expression of miR-181a, miR-200c and miR-210 in a Three-dimensional-specific Manner in DLD-1 Colorectal Cancer Cells", Anticancer Research, vol. 32, No. 6, Jun. 1, 2012, pp. 2271-2275.
Ingram, M., et al., "Tissue engineered tumor models", Biotechnic & Histochemistry, vol. 85, No. 4, 2010, pp. 213-229.

* cited by examiner

*Primary Examiner* — Richard A Schnizer
(74) *Attorney, Agent, or Firm* — Ladas & Parry LLP

(57) ABSTRACT

A method for identifying a cluster or sub-cluster of microRNAs (miRNAs) that provides a signature profile for differentiating cells grown in one type of culture model from cells grown in another type of culture model. Also, kits and methods for evaluating, selecting, and/or characterizing tissue culture models using the miRNA profiles and a cluster or sub-cluster of miRNAs that provides the signature profile. Also, a method for identifying a putative mRNA target of a miRNA for evaluating and targeting with a drug candidate by using the cluster or sub-cluster of miRNAs and a method for selecting a culture model for use as a drug platform for screening a candidate molecule for activity against tumor cells in tumor stroma.

19 Claims, 22 Drawing Sheets
Specification includes a Sequence Listing.

miR_Cluster 19 and 27: Angiogenic miRNA Gene expression Target network

SEQUENCE LISTING

```
<160> NUMBER OF SEQ ID NOS: 16

<210> SEQ ID NO 1
<211> LENGTH: 17
<212> TYPE: DNA
<213> ORGANISM: HOMO SAPIENS
<220> FEATURE:
<221> NAME/KEY: misc_feature
<222> LOCATION: (1)..(17)
<223> OTHER INFORMATION: Chromosome active sequence corresponding to
      miRNA Accession No.MIMAT0004784

<400> SEQUENCE: 1
gtgtatatgc ccatgga                                                    17

<210> SEQ ID NO 2
<211> LENGTH: 20
<212> TYPE: DNA
<213> ORGANISM: HOMO SAPIENS
<220> FEATURE:
<221> NAME/KEY: misc_feature
<222> LOCATION: (1)..(20)
<223> OTHER INFORMATION: Chromosome active sequence corresponding to
      miRNA Accession No.MIMAT0000281

<400> SEQUENCE: 2
aacggaacca ctagtgactt                                                 20

<210> SEQ ID NO 3
<211> LENGTH: 16
<212> TYPE: DNA
<213> ORGANISM: HOMO SAPIENS
<220> FEATURE:
<221> NAME/KEY: misc_feature
<222> LOCATION: (1)..(16)
<223> OTHER INFORMATION: Chromosome active sequence corresponding to
      miRNA Accession No.MIMAT0000426

<400> SEQUENCE: 3
cgaccatggc tgtaga                                                     16

<210> SEQ ID NO 4
<211> LENGTH: 19
<212> TYPE: DNA
<213> ORGANISM: HOMO SAPIENS
<220> FEATURE:
<221> NAME/KEY: misc_feature
<222> LOCATION: (1)..(19)
<223> OTHER INFORMATION: Chromosome active sequence corresponding to
      miRNA Accession No.MIMAT0000097
```

```
<400> SEQUENCE: 4
cacaagatcg gatctacgg                                                  19

<210> SEQ ID NO 5
<211> LENGTH: 20
<212> TYPE: DNA
<213> ORGANISM: HOMO SAPIENS
<220> FEATURE:
<221> NAME/KEY: misc_feature
<222> LOCATION: (1)..(20)
<223> OTHER INFORMATION: Chromosome active sequence corresponding to
      miRNA Accession No.MIMAT0001080

<400> SEQUENCE: 5
cccaacaaca ggaaactacc                                                 20

<210> SEQ ID NO 6
<211> LENGTH: 19
<212> TYPE: DNA
<213> ORGANISM: HOMO SAPIENS
<220> FEATURE:
<221> NAME/KEY: misc_feature
<222> LOCATION: (1)..(19)
<223> OTHER INFORMATION: Chromosome active sequence corresponding to
      miRNA Accession No.MIMAT0002809

<400> SEQUENCE: 6
agcctatgga attcagttc                                                  19

<210> SEQ ID NO 7
<211> LENGTH: 13
<212> TYPE: DNA
<213> ORGANISM: HOMO SAPIENS
<220> FEATURE:
<221> NAME/KEY: misc_feature
<222> LOCATION: (1)..(13)
<223> OTHER INFORMATION: Chromosome active sequence corresponding to
      miRNA Accession No.MIMAT0000457

<400> SEQUENCE: 7
ccctccacca tgc                                                        13

<210> SEQ ID NO 8
<211> LENGTH: 13
<212> TYPE: DNA
<213> ORGANISM: HOMO SAPIENS
<220> FEATURE:
<221> NAME/KEY: misc_feature
<222> LOCATION: (1)..(13)
<223> OTHER INFORMATION: Chromosome active sequence corresponding to
      miRNA Accession No.MIMAT0000447

<400> SEQUENCE: 8
cccctctggt caa                                                        13

<210> SEQ ID NO 9
<211> LENGTH: 18
<212> TYPE: DNA
<213> ORGANISM: HOMO SAPIENS
<220> FEATURE:
<221> NAME/KEY: misc_feature
<222> LOCATION: (1)..(18)
<223> OTHER INFORMATION: Chromosome active sequence corresponding to
      miRNA Accession No.MIMAT0005880

<400> SEQUENCE: 9
tccctgatcc aaaaatcc                                                   18
```

```
<210> SEQ ID NO 10
<211> LENGTH: 16
<212> TYPE: DNA
<213> ORGANISM: HOMO SAPIENS
<220> FEATURE:
<221> NAME/KEY: misc_feature
<222> LOCATION: (1)..(16)
<223> OTHER INFORMATION: Chromosome active sequence corresponding to
      miRNA Accession No.MIMAT0005898

<400> SEQUENCE: 10
cctgctccaa aaatcc                                                      16

<210> SEQ ID NO 11
<211> LENGTH: 17
<212> TYPE: DNA
<213> ORGANISM: HOMO SAPIENS
<220> FEATURE:
<221> NAME/KEY: misc_feature
<222> LOCATION: (1)..(17)
<223> OTHER INFORMATION: Chromosome active sequence corresponding to
      miRNA Accession No.MIMAT0003299

<400> SEQUENCE: 11
accttccctg gtacaga                                                     17

<210> SEQ ID NO 12
<211> LENGTH: 17
<212> TYPE: DNA
<213> ORGANISM: HOMO SAPIENS
<220> FEATURE:
<221> NAME/KEY: misc_feature
<222> LOCATION: (1)..(17)
<223> OTHER INFORMATION: Chromosome active sequence corresponding to
      miRNA Accession No.MIMAT0000646

<400> SEQUENCE: 12
acccctatca cgattag                                                     17

<210> SEQ ID NO 13
<211> LENGTH: 23
<212> TYPE: DNA
<213> ORGANISM: HOMO SAPIENS
<220> FEATURE:
<221> NAME/KEY: misc_feature
<222> LOCATION: (1)..(23)
<223> OTHER INFORMATION: Chromosome active sequence corresponding to
      miRNA Accession No.MIMAT0000448

<400> SEQUENCE: 13
tccatcatca aacaaatgg agt                                               23

<210> SEQ ID NO 14
<211> LENGTH: 20
<212> TYPE: DNA
<213> ORGANISM: HOMO SAPIENS
<220> FEATURE:
<221> NAME/KEY: misc_feature
<222> LOCATION: (1)..(20)
<223> OTHER INFORMATION: Chromosome active sequence corresponding to
      miRNA Accession No.MIMAT0002890

<400> SEQUENCE: 14
atgtatgtgg gacggtaaac                                                  20

<210> SEQ ID NO 15
<211> LENGTH: 16
```

```
<212> TYPE: DNA
<213> ORGANISM: HOMO SAPIENS
<220> FEATURE:
<221> NAME/KEY: misc_feature
<222> LOCATION: (1)..(16)
<223> OTHER INFORMATION: Chromosome active sequence corresponding to
      miRNA Accession No.MIMAT0000736

<400> SEQUENCE: 15
acagagagct tgccct                                                       16

<210> SEQ ID NO 16
<211> LENGTH: 18
<212> TYPE: DNA
<213> ORGANISM: HOMO SAPIENS
<220> FEATURE:
<221> NAME/KEY: misc_feature
<222> LOCATION: (1)..(18)
<223> OTHER INFORMATION: Chromosome active sequence corresponding to
      miRNA Accession No.MIMAT0003180

<400> SEQUENCE: 16
aagtggatga ccctgtac                                                     18
```

KITS AND METHODS FOR EVALUATING, SELECTING AND CHARACTERIZING TISSUE CULTURE MODELS USING MICRO-RNA PROFILES

CROSS-REFERENCE TO RELATED APPLICATIONS

This U.S. application claims priority under 35 U.S.C. 371 to, and is a U.S. National Phase application of, the International Patent Application No. PCT/US2014/031362, filed 20 Mar. 2014 which claims priority from U.S. Patent Application 61/803,579 filed Mar. 20, 2013; U.S. Patent Application 61/845,150 filed Jul. 11, 2013; and U.S. Patent Application 61/857,903 filed Jul. 24, 2013, which are incorporated herein by reference in their entirety.

FIELD OF THE INVENTION

The invention is related to a method for identifying a cluster or sub-cluster of microRNAs (miRNAs) that provides a signature profile for differentiating cells grown in one type of culture model from cells grown in another type of culture model, and to kits and methods for evaluating, selecting, and/or characterizing tissue culture models using the miRNA profiles. The invention is also related to a cluster or sub-cluster of miRNAs that provides the signature profile. The invention is further related to a method for identifying a putative mRNA target of a miRNA for evaluation and targeting with a drug candidate by using the cluster or sub-cluster of miRNAs. The invention is still further related to selecting a culture model for use as a drug platform for screening a candidate molecule for activity against tumor cells in tumor stroma.

BACKGROUND OF THE INVENTION

Many research programs use well-established tumor cell lines as tumor models for in vitro drug screening studies. Because the tumor spheroids, tumor cells grown as three-dimensional (3-D) structures are multicellular more like the tumors in vivo than monolayer culture cells, use of tumor cell spheroids as in vitro models for drug development is of great interest. Monotypic spheroids, however, do not model the stromal-epithelial interactions that have an important role in controlling tumor growth and development in vivo.

The tissue engineering lab at Huntington Medical Research Institutes (HMRI) in Pasadena, Calif. under the direction of Dr. Marylou Ingram discovered a method for generating, reproducibly, more realistic 3-D tumor models that contain both stromal and malignant epithelial cells with an architecture that closely resembles tumor micro-lesions in vivo. Because they are so tissue-like they are referred to as tumor histoids. The bioreactor developed to generate histoid constructs is described and illustrated in U.S. Pat. No. 6,998,264, the contents of which are incorporated herein by reference. Examples of histological sections of tumor histoids representing cancers of breast, prostate, colon, pancreas and urinary bladder are described.

The 3D heterocellular tumor histoids, produced with no scaffolds or extracellular matrix addition, allow the cells to contact each other in a way very similar to cells in natural tumors. These contacts enable development of a stromal microenvironment that closely approximates the in vivo environment of natural tumors. Therefore 3D tumor histoids potentially provide a significant advantage over 2D monolayer cultures typically used for studies of cancer biology and for pre-clinical drug screening, testing and development. However such multicellular 3D models are currently used as drug testing platforms without thorough molecular characterization that would be advantageous for evaluation of their use for modeling of in vivo treatment conditions in place of 2D monolayer cultures. In addition it is not known whether the in vitro 3D models produced by different methods, for example by low shear microgravity or high throughput hanging drop, are molecularly similar or identical. The present invention is based at least in part on the recognition that this information would be useful for eliminating variability in the use of these models for drug testing. Furthermore, the inventor recognized that delineating the molecular characteristics unique to 3D cultures could yield both diagnostic and therapeutic targets that are superior to those identified through molecular characterization of 2D monolayer cultures as compared to healthy cells. Thus molecular characterization of the features that uniquely distinguish these 3D in vitro model products has heretofore constituted an unmet need.

In recent years the mature small RNAs, termed the microRNAs (miRNAs) have emerged as important biological regulatory molecules playing a pivotal role in gene expression of plants and animals, including humans. miRNAs are integral part of miRNA-protein RISC complex that regulates messenger RNAs (mRNAs) at translational level through binding target mRNAs at their 3' untranslated region (3'UTR). A single miRNA can regulate expression of multiple genes and thus act as a global modulator of diverse cellular and biological processes. Moreover miRNA expression profile can be indicative of physiological state of a cell. For example the expression profiles of a few hundred miRNA have provided more specific classification of human cancers than mRNA profiles (Lu, J., et al., Nature, 2005, 435(7043), 834-838). Unique expression profiles identified in lung cancers position miRNA as diagnostic and prognostic markers (Yanaihara, N., et al., Cancer Cell, 2006, 9(3), 189-198).

The prior art studies however did not attempt to elucidate the biological significance of changes in miRNA expression profile in vitro tumor model tissues.

The present invention is based at least in part on the recognition that such a study would allow for identification of cellular pathways whose dysregulation underlies tumor development and maintenance. The inventor also recognized that this kind of analysis would be useful in characterizing the differences between 3D heterocellular tumor histoids and 2D monolayer cultures of cancer cells, since it would allow for delineation of the molecular features that are unique to the biology of 3D culture micro-tissues, and that are more likely to be present in natural tumors. The inventor further recognized that pathways so identified could provide superior diagnostic and therapeutic candidates as compared with pathways identified in comparison of healthy cells and 2D monolayer cultures of cancer cells. Moreover, the inventor recognized that, if a given signaling pathway is found to be dysregulated in a particular tumor, knowing its status as unique to 3D cultures or common to both 3D and 2D cultures would allow for an informed decision as to which system to use as the drug development platform. Since using 3D cultures is significantly more costly, an informed choice could result in significant savings in cost and possibly time. Thus, the inventor recognized that proper characterization of miRNAs and cellular pathways unique to 3D heterocellular tumor histoid could go a long way to satisfying the need described above.

SUMMARY OF THE INVENTION

In accordance with a first embodiment of the invention, there is provided a method comprising identifying a cluster or sub-cluster of miRNAs that provides a signature profile for differentiating cells grown in 3D multicellular culture from cells grown in 2D monolayer culture or for differentiating cells grown in one type of 3D multicellular culture from cells grown in another type of 3D multicellular culture. In a preferred aspect of this embodiment, the method comprises the steps of:
  (a) comparing a first miRNA expression profile of normal and/or tumor cells grown in a 3D multicellular culture to a second miRNA expression profile of the normal and/or tumor cells grown in a 2D monolayer culture or in another type of 3D multicellular culture; and
  (b) identifying a cluster or sub-cluster of miRNAs selected from the group consisting of (i) miRNAs in the first expression profile that are down regulated in the second expression profile; (ii) miRNAs down regulated in the first expression profile that are up regulated in the second expression profile; (iii) miRNAs detected in the first expression profile that are up or down regulated in the first expression profile as compared with the second expression profile; and (iv) a combination thereof.

In one aspect of this embodiment, the method comprises searching a miRNA gene target database to correlate at least one of the miRNAs in the cluster or sub-cluster with a mRNA target of known function to ascertain a role of the at least one miRNA in a gene expression network. In another aspect of this embodiment, the miRNAs in the cluster or sub-cluster are evaluated in a sample tissue of a patient's breast or prostate solid tumor. In yet another aspect of this embodiment, the miRNAs in the cluster or sub-cluster are evaluated in a normal and tumor tissue segment of a patient's solid tumor. In a further aspect of this embodiment, the method includes selecting a 3D multicellular culture model or 2D monolayer culture for further drug screening, testing and development based on the identifying in step (b).

In a second embodiment of the invention, there is provided a kit comprising:
  (a) a tissue culture model for in vitro growth of normal and/or tumor cells; and
  (b) an alphanumeric label associated with the tissue culture model that characterizes the tissue culture model based on a pattern in which a cluster of miRNAs is expressed when the normal and tumor cells are grown in the tissue culture model. In a preferred aspect of this embodiment, the tissue culture model comprises a multicellular culture and the label characterizes the tissue culture model at least in part based on a level of expression of the miRNAs when the normal and tumor cells are grown in the tissue culture model relative to a level of expression of the miRNAs when the normal and tumor cells are grown in monolayer cells or in a different multicellular culture.

In a more preferred aspect of this embodiment, the label characterizes the tissue culture model at least in part by (i) a level of the miRNA expression in multicellular culture relative to monolayer cells; (ii) a similarity or dissimilarity of the miRNA expression in the tumor cells and in normal cells; and (iii) if the miRNA expression in the tumor cells and in normal cells is dissimilar, whether a shift from monolayer cells to multicellular culture causes a change in the level of the miRNA expression in cells selected from the group consisting of normal cells, breast tumor cells, prostate tumor cells and a combination thereof.

In another preferred aspect of this embodiment, the alphanumeric label characterizes a cluster pattern of miRNA profile in the tissue culture model as a type selected from the group consisting of:
  (a) a first type wherein expression of the miRNAs is down regulated or not detected when the tumor cells and normal cells are grown in monolayer culture and is up regulated and significant as a fold change of at least 1.5 when the tumor cells and normal cells are grown in multicellular culture;
  (b) a second type wherein expression of the miRNAs is up regulated when the tumor cells and normal cells are grown in monolayer cells and is down regulated and significant as a fold change of at least 1.5 when the tumor cells and the normal cells are grown in multicellular culture;
  (c) a third type wherein expression of the miRNAs is down regulated when the tumor cells and normal cells are grown in monolayer cells and is up regulated and significant as a fold change of at least 1.5 in the normal cells, but not in breast tumor cells or prostate tumor cells, when grown in multicellular culture;
  (d) a fourth type wherein expression of the miRNAs is up regulated when the tumor cells and the normal cells are grown in monolayer cells and is down regulated and significant as a fold change of at least 1.5 in the normal cells, but not the breast tumor cells or prostate tumor cells, when grown in multicellular culture;
  (e) a fifth type wherein expression of the miRNAs is down regulated when the tumor cells and normal cells are grown in monolayer cells and is up regulated and significant as a fold change of at least 1.5 in the breast tumor cells, but not the normal cells or prostate tumor cells, when grown in multicellular culture;
  (f) a sixth type wherein expression of the miRNAs is up regulated when the tumor cells and the normal cells are grown in monolayer cells and is down regulated and significant as a fold change of at least 1.5 in the breast tumor cells, but not the normal cells or prostate tumor cells, when grown in multicellular culture;
  (g) a seventh type wherein expression of the miRNAs is down regulated when the tumor cells and the normal cells are grown in monolayer cells and is up regulated and significant as a fold change of at least 1.5 in the prostate tumor cells, but not the normal cells or breast tumor cells, when grown in multicellular culture;
  (h) an eighth type wherein expression of the miRNAs is up regulated when the tumor cells and the normal cells are grown in monolayer cells and is down regulated and significant as a fold change of at least 1.5 in the prostate tumor cells, but not the normal cells or breast tumor cells, when grown in multicellular culture;
  (i) a ninth type wherein expression of the miRNAs is down regulated when the tumor cells and the normal cells are grown in monolayer cells and is up regulated and significant as a fold change of at least 1.5 in the normal cells and breast tumor cells, but not the prostate tumor cells, when grown in multicellular culture;
  (j) a tenth type wherein expression of the miRNAs is up regulated when the tumor cells and the normal cells are grown in monolayer cells and is down regulated and significant as a fold change of at least 1.5 in the normal cells and breast tumor cells, but not the prostate tumor cells, when grown in multicellular culture;
  (k) an eleventh type wherein expression of the miRNAs is down regulated when the tumor cells and the normal cells are grown in monolayer cells and is up regulated and significant as a fold change of at least 1.5 in the normal cells and the prostate tumor cells, but not the breast tumor cells, when grown in multicellular culture;

(l) a twelfth type wherein expression of the miRNAs is up regulated when the tumor cells and the normal cells are grown in monolayer cells and is down regulated and significant as a fold change of at least 1.5 in the normal cells and the prostate tumor cells, but not the breast tumor cells, are grown in multicellular culture;

(m) a thirteenth type wherein expression of the miRNAs is down regulated when the tumor cells and the normal cells are grown in monolayer cells and is up regulated and significant as a fold change of at least 1.5 in the breast tumor cells and the prostate tumor cells, but not the normal cells, when grown in multicellular culture; and (n) a fourteenth type wherein expression of the miRNA is up regulated when the tumor cells and the normal cells are grown in monolayer cells and is down regulated and the decrease is significant as a fold change of at least 1.5 in the breast tumor cells and the prostate tumor cells, but not the normal cells, when grown in multicellular culture.

In a third embodiment of the invention, there is provided a method for selecting a tissue culture model for screening a drug candidate for activity against tumor cells, the method comprising the steps of:

(a) comparing an expression profile of a cluster or sub-cluster of miRNAs wherein the tumor cells and normal cells are grown in a first tissue culture model with an expression profile of the cluster or sub-cluster of miRNAs wherein the tumor cells and the normal cells are grown in a second tissue culture model; and (b) selecting between the first tissue culture model and the second tissue culture model for screening of the drug candidate based on the comparing in step (a). In a preferred aspect, the method may comprise screening the drug candidate with the tissue culture model selected in step (b). In another preferred aspect, the first tissue culture model comprises monolayer cells and the second tissue culture model comprises multicellular cells.

In a fourth embodiment of the invention, there is provided a method comprising providing a drug platform for screening a candidate molecule for possible activity against tumor cells, wherein the tumor cells are grown in a culture model and the candidate molecule is then administered to the tumor cells grown in the culture model and an assay is conducted to look for anti-tumor activity, and wherein the culture model is selected based on a pattern in which a cluster or sub-cluster of miRNAs is expressed when the tumor cells are grown in the culture model.

In a preferred aspect of this embodiment, the tissue culture model comprises a multicellular culture and the tissue culture model is selected at least in part based on a level of expression of the miRNAs when the tumor cells are grown in the tissue culture model relative to a level of expression of the miRNAs when the tumor cells are grown in monolayer cells or in a different multicellular culture. In another preferred aspect, the tissue culture model is selected at least in part by (i) a level of the miRNA expression in multicellular culture relative to monolayer cells; (ii) a similarity or dissimilarity of the miRNA expression in the tumor cells and in normal cells; and (iii) if the miRNA expression in the tumor cells and in normal cells is dissimilar, whether a shift from monolayer cells to multicellular culture causes a change in the level of the miRNA expression in cells selected from the group consisting of normal cells, breast tumor cells, prostate tumor cells and a combination thereof.

In yet another preferred aspect of this embodiment, the tissue culture model is a type selected from the group consisting of:

(a) a first type wherein expression of the miRNAs is down regulated when the tumor cells and normal cells are grown in monolayer cells and is up regulated and significant as a fold change of at least 1.5 in the tumor cells and normal cells, when grown in multicellular culture;

(b) a second type wherein expression of the miRNAs is up regulated when the tumor cells and normal cells are grown in monolayer cells and is down regulated and significant as a fold change of at least 1.5 win the tumor cells and the normal cells, when grown in multicellular culture;

(c) a third type wherein expression of the miRNAs is down regulated when the tumor cells and normal cells are grown in monolayer cells and is up regulated and significant as a fold change of at least 1.5 in the normal cells, but not breast tumor cells or prostate tumor cells, when grown in multicellular culture;

(d) a fourth type wherein expression of the miRNAs is up regulated when the tumor cells and the normal cells are grown in monolayer cells and is down regulated and significant as a fold change of at least 1.5 in the normal cells, but not the breast tumor cells or prostate tumor cells, when grown in multicellular culture;

(e) a fifth type wherein expression of the miRNAs is down regulated when the tumor cells and normal cells are grown in monolayer cells and is up regulated and significant as a fold change of at least 1.5 in the breast tumor cells, but not the normal cells or prostate tumor cells, when grown in multicellular culture;

(f) a sixth type wherein expression of the miRNAs is up regulated when the tumor cells and the normal cells are grown in monolayer cells and is down regulated and significant as a fold change of at least 1.5 in the breast tumor cells, but not the normal cells or prostate tumor cells, when grown in multicellular culture;

(g) a seventh type wherein expression of the miRNAs is down regulated when the tumor cells and the normal cells are grown in monolayer cells and is up regulated and significant as a fold change of at least 1.5 in the prostate tumor cells, but not the normal cells or breast tumor cells, when grown in multicellular culture;

(h) an eighth type wherein expression of the miRNAs is up regulated when the tumor cells and the normal cells are grown in monolayer cells and is down regulated and significant as a fold change of at least 1.5 in the prostate tumor cells, but not the normal cells or breast tumor cells, when grown in multicellular culture;

(i) a ninth type wherein expression of the miRNAs is down regulated when the tumor cells and the normal cells are grown in monolayer cells and is up regulated and significant as a fold change of at least 1.5 in the normal cells and breast tumor cells, but not the prostate tumor cells, when grown in multicellular culture;

(j) a tenth type wherein expression of the miRNAs is up regulated when the tumor cells and the normal cells are grown in monolayer cells and is down regulated and significant as a fold change of at least 1.5 in the normal cells and the breast tumor cells, but not the prostate tumor cells, when grown in multicellular culture;

(k) an eleventh type wherein expression of the miRNAs is down regulated when the tumor cells and the normal cells are grown in monolayer cells and is up regulated and significant as a fold change of at least 1.5 in the normal cells and the prostate tumor cells, but not the breast tumor cells, when grown in multicellular culture;

(l) a twelfth type wherein expression of the miRNAs is up regulated when the tumor cells and the normal cells are grown in monolayer cells and is down regulated and significant as a fold change of at least 1.5 in the normal cells and the prostate tumor cells, but not the breast tumor cells, when grown in multicellular culture;

(m) a thirteenth type wherein expression of the miRNAs is down regulated when the tumor cells and the normal cells are grown in monolayer cells and is up regulated and significant as a fold change of at least 1.5 in the breast tumor cells and the prostate tumor cells, but not the normal cells, when grown in multicellular culture; and (n) a fourteenth type wherein expression of the miRNA is up regulated when the tumor cells and the normal cells are grown in monolayer cells and is down regulated and significant as a fold change of at least 1.5 in the breast tumor cells and the prostate tumor cells, but not the normal cells, when are grown in multicellular culture.

In a fourth embodiment of the invention, there is provided a method for identifying a putative mRNA target for evaluation with a drug candidate, the method comprising the steps of:

(a) identifying a cluster or sub-cluster of miRNAs that are expressed with a distinct profile (i) in tumor and/or normal cells cultured in multicellular tissue culture as compared with the tumor and/or normal cells cultured in monolayer cells and (ii) in a first type of tumor cells cultured in the multicellular tissue culture as compared with normal cells and/or another type or types of tumor cells cultured in the multicellular tissue culture;

(b) correlating the miRNAs in the cluster or sub-cluster with at least one mRNA target having a known gene expression;

(c) correlating the known gene expression with a known gene interaction network of cellular processes; and (d) selecting the at least one mRNA target for evaluation based on the correlation in step (c).

In a preferred aspect of this embodiment, the cluster or sub-cluster of miRNAs are expressed with a distinct profile in tumor cells grown in the multicellular tissue culture as compared with normal cells grown in the multicellular tissue culture. In another preferred aspect, the cluster or sub-cluster of miRNAs are expressed with a distinct profile in breast tumor cells grown in the multicellular tissue culture as compared with prostate tumor cells grown in the multicellular tissue culture.

In yet another preferred aspect of this embodiment, the gene interaction network is for cellular processes selected from the group consisting of (i) epigenetics; (ii) inflammation; (iii) apoptosis and (iii) angiogenesis, and is preferably for cellular processes selected from the group consisting of (i) chromatin architecture maintenance and modifications; (ii) inflammatory NF-kappaB cascade; and (iii) negative regulation of apoptosis. In a still further preferred embodiment, the drug candidate is an anti-miR, siRNA or a small molecule to target a product of the gene expression.

In a fifth embodiment of the invention, there is provided a cluster or sub-cluster of nucleic acids that provide an expression profile for differentiating cells grown in 3D multicellular culture from cells grown in 2D monolayer culture or cells grown in one type of 3D multicellular culture from cells grown in another type of 3D multicellular culture.

The cluster or sub-cluster of nucleic acids comprise the miRNAs described herein below and complementary nucleic acids that are complements of the respective nucleotide sequences of the miRNAs described herein below, wherein the respective complements and nucleotide sequences consist of the same number of nucleotides and are 100% complementary.

BRIEF DESCRIPTION OF THE DRAWINGS

FIG. 7 differentiated normal and breast cancer from prostate cancer; 6 miRNAs in sub-cluster 1-3-32 (FIG. 8) differentiated 3Ds from 2Ds and histoids from spheroids; and 5 miRNAs in sub-cluster 2-3-32 differentiated cancer from the normal.

DETAILED DESCRIPTION

Figure 1:
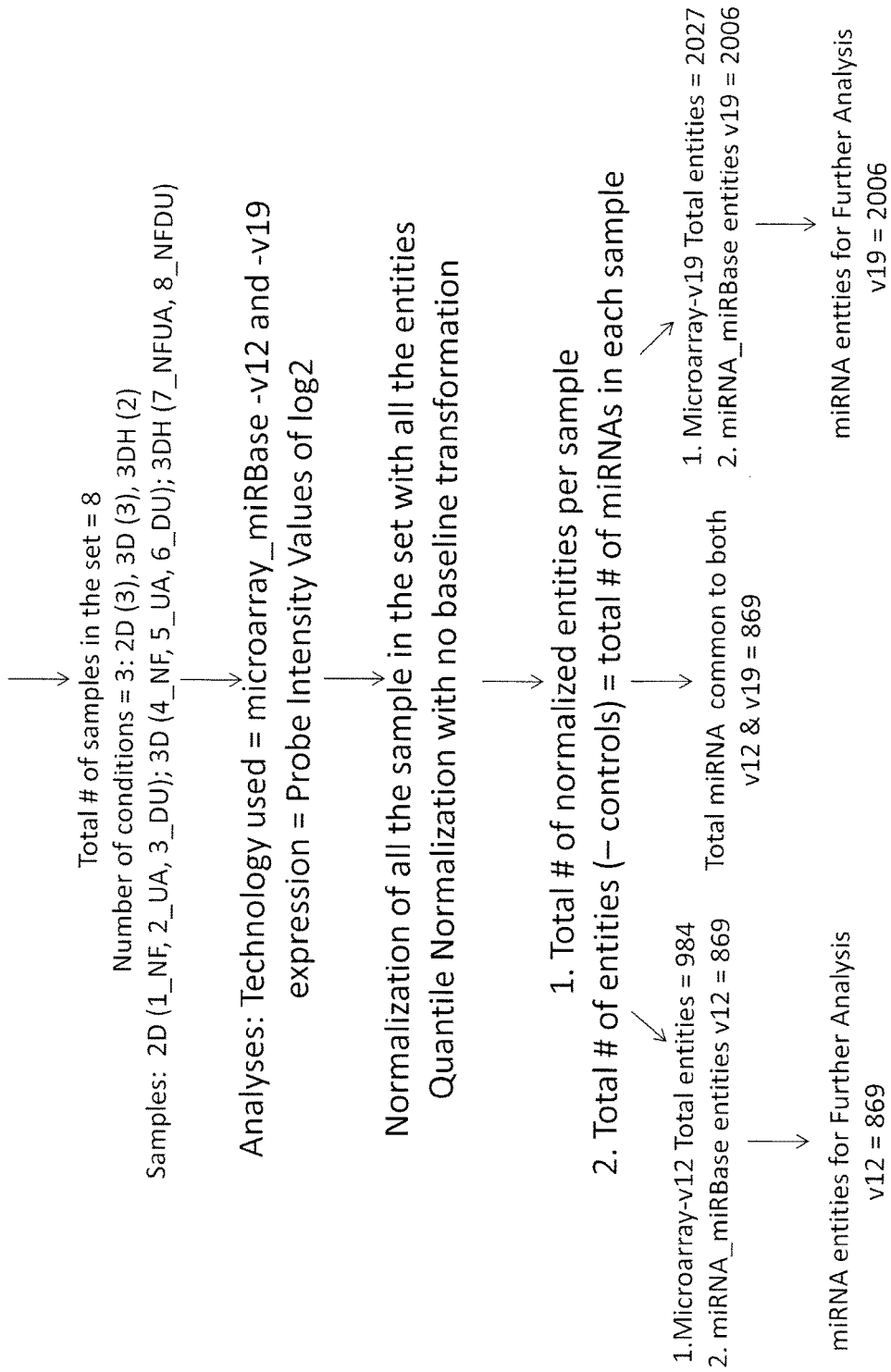
FIG. 1 shows part I of the analytical workflow of normalization of log 2 based miRNA expression values of 984 miRNA entities in human microarray miRBase version v12 and 2027 miRNA in version v19; and then filtering out the controls (and other viral miRNA in v12) across all the 8 samples by two way Venn diagram which yielded a total filtered entity list of 869 miRNA in v12 (that was common to v19) and a total entity list of 2006 miRNA in v19. which were further used in miRNA signature profile pattern development.

In an effort to characterize and delineate in vivo like biology of 3D tumor models, the inventor initiated a molecular profiling study of 3D model tumor tissue (see "Snapshot of Epigenetic Modifiers in 3D Model Tumor Tissue" in Experimental section below). As exemplified in the study, miRNA profiling revealed distinct miRNA signature that simultaneously differentiates cells along two axes: normal and cancer cells, and the cells that were grown in either 3D or 2D culture conditions. The analysis of the targets of the signature miRNAs pointed to chromatin modification as one of the significant signaling pathways affected in the 3D shift of 2D cells in cancer cells (breast, prostate) as opposed to similar shift of normal cells (foreskin fibroblast). This result was affirmed in gene expression analysis. The changes in expression of histone modifier gene transcripts and their protein status predicted by miRNA signature analysis can be further validated using standard methods to ascertain significance of chromatin modifications in 3D tumor tissue models. Similar methods can be used with 3D cultures produced by alternative means such as Perfecta 3D™ Hanging Drop Culture plates, a system that is particularly well suited for high throughput screening in cancer drug development.

The inventor also initiated a bioinformatics analysis of v12 miRNA profiles in normal and tumor spheroids and histoids that revealed a 3D-specific miRNA signature profile of 16 miRNAs (cluster 3-32) that differentiated these cells from cells cultured in 2D (see "MicroRNA Integrated Gene Expression Interaction Network Profiles in 3D Tumor Tissue Models" in the Experimental section below). The signature miRNA profiles when integrated with their mRNA targets and gene expression revealed that the signature miRNAs specifically target genes that are involved in the regulatory network of several important cellular processes. At the first step, three subsets of signature miRNAs that differentiated prostate cancer cells from normal cells and breast cancer cells (5 miRNAs, cluster 0-3-32), 3D cultures from 2D cultures and histoids from spheroids (6 miRNAs, cluster 1-3-32), and normal cells from culture cells (5 miRNAs, cluster 2-3-32) have been identified. The target integration analysis was subsequently carried out to relate and integrate miRNA(s) to their mRNA target(s) and expressed genes. The results revealed that each cluster significantly associates with distinct a set of genes. Thus cluster 0-3-32 strongly associated with chromatin architecture maintenance and modifications, cluster 1-3-32 strongly associated with inflammatory NF-kappaB cascade, and cluster 2-3-32 is strongly associated with negative regulation of apoptosis in the 3D shift of 2D tumor and normal cells. This highlights the importance of miRNA integrated target gene expression interactions network profiling approach in molecular characterization of tumor tissues models. Other miRNA integrated target gene expression, interactions and network profile analyses in 3D tumor tissue models identified additional cellular processes that distinguish 3D cultures. These include epigenetics, inflammation, apoptosis, angiogenesis and others. These data provide a basis for cancer drug screening and developing targeted therapeutics and diagnostics.

The methods described herein can be used to the address the question such as "do hanging drop (HD) models have the same signature as bioreactor model or is the signature different?" This inquiry is important, especially for epigenetic drugs since the use of HDs as high-through-put (HTP) platforms for drug development is much more feasible than bioreactor method for HTP screening.

The above method of defining miRNA signatures and integrating so identified miRNAs with their known targets can be also used for differentiation between multiple cultures along several axes at once (for example tumorigenicity, invasiveness, culture conditions), and for identification of signaling pathways that underlie these properties. This information may be used to target specific mRNA/miRNA set with antimiRs (which are used in vivo as drugs) to effect a change in the GE network or pathways. This approach is particularly advantageous because perturbations in a single miRNA and/or a set, may perturb an entire GE network, and through it affect function-altering protein levels leading to metabolic changes to ultimately achieve a systemic effect in vivo. Therefore rather than targeting a single mRNA or protein, the invention opens up the possibility that, with targeting a single miRNA or a set thereof, one can discover how a GE network is affected, and if it is translatable to in vivo understanding.

Furthermore, the 3D models described herein are particularly well suited for pre-clinical studies and evaluations aimed at understanding how perturbations in a single miRNA and/or a set may perturb a GE network to have a systemic effect in vivo.

This information may also be used to determine an appropriate tissue culture model for a drug platform. Thus, it is known that a 3D cell-cell interaction is a different environment than 2D cell-cell interaction. With the provision of a set of miRNAs that differentiate 3D from 2D in the context of normal vs cancer which target, for example, an epigenetic network, it is possible to determine whether, and in what circumstances, a 3D culture would be a more relevant platform for epigenetic drug development than 2D, or, alternatively, when it would suffice to use 2D culture with specificity for drug testing.

The v12 miRNA microarray platform (961 miR entities) used in the Experimental section below was based on miRBase version 12 (2009-2010), which means that all of these miRNAs were known and documented in the database at the time of that study. The database has grown since and, recently, the inventor analyzed the same samples with a more recent microarray platform (which has over 2000 miRNA entities) based on miRBase version 19. Using the expanded array the inventor has identified other miRs that also add to the signature by bioinformatics analyses. These miRNAs are based on the entities listed in the miRBase versions used for microarray analyses at the time the analyses were done. It may be appreciated that the same analysis may be done with microarray platforms based on newer databases when they become available.

As described above, in one embodiment, the invention comprises a cluster or sub-cluster of nucleic acids that provide an expression profile for differentiating cells grown in 3D multicellular culture from cells grown in 2D monolayer culture or cells grown in one type of 3D multicellular culture from cells grown in another type of 3D multicellular culture. It may be appreciated that the identification of the described clusters or sub-clusters of miRNAs of known sequence also provides identification of a cluster or subcluster of complementary nucleic acids having sequences that are complements of the respective nucleotide sequences of the miRNAs in the clusters or sub-clusters, wherein the respective complementary sequences and nucleotide sequences consist of the same number of nucleotides and are 100% complementary. Such complementary nucleic acid sequences also form part of the invention described herein.

EXPERIMENTAL METHODS AND RESULTS

Tools

The following tools are known by and are publicly and/or commercially available to those of skill in the art for performing miRNA and GE analysis in connection with the methods and kits described herein:
1. The miRBase database: a searchable database of published miRNA sequences and annotation. Each entry in the miRBase Sequence database represents a predicted hairpin portion of a miRNA transcript (termed mir in the database), with information on the location and sequence of the mature miRNA sequence (termed miR). Both hairpin and mature sequences are available for searching and browsing, and entries can also be retrieved by name, keyword, references and annotation. All sequence and annotation data are also available for download. The miRBase Registry provides miRNA gene hunters with unique names for novel miRNA genes prior to publication of results. miRBase is hosted and maintained in the Faculty of Life Sciences at the University of Manchester with funding from the BBSRC, and was previously hosted and supported by the Wellcome Trust Sanger Institute.
2. TargetScan: predicts biological targets of miRNAs by searching for the presence of conserved 8mer and 7mer sites that match the seed region of each miRNA. As an option, nonconserved sites are also predicted. Also identified are sites with mismatches in the seed region that are compensated by conserved 3' pairing. In mammals, predictions are ranked based on the predicted efficacy of targeting as calculated using the context+ scores of the sites. As an option, predictions are also ranked by their probability of conserved targeting. TargetScanHuman considers matches to annotated human UTRs and their orthologs, as defined by UCSC whole-genome alignments. Conserved targeting has also been detected within open reading frames (ORFs). This search page of TargetScan Release 6.2 retrieves predicted regulatory targets of mammalian microRNAs. Many targets are the same as those presented in previous versions of the TargetScan site (Releases 2.0, 2.1, 3.0, 3.1, 4.0-4.2, 5.0-5.2, and 6.0). Compared to previous releases, Release 6 extends context score contributions to include seed-pairing stability and target-site abundance, includes all 3' UTRs from RefSeq (rather than just the longest UTR from each gene), and includes more miRNA families.
3. The Gene Ontology project: a major bioinformatics initiative with the aim of standardizing the representation of gene and gene product attributes across species and databases. The collection of tools developed by the GO Consortium and by third parties and available on the Gene Ontology website includes tools for the following categories:
    Ontology or annotation browser
    Ontology or annotation search engine
    Ontology or annotation visualization
    Ontology or annotation editor
4. Agilent Technologies: provides a full range of bioinformatics software tools to enable robust visualization and analysis of genomic datasets across a range of applications. Agilent's GeneSpring software is commercially available for gene expression analysis, miRNA and splicing analysis, including
    Integrated platform for multi-omic data analysis
    Transcriptomic analysis
    Genomic copy number analysis
    Genome-wide association analysis
    Built-in ID browser automates database and spectral library searches
    Comprehensive analytical and visualization toolkit
    Statistical tools for testing differential expression
    Pattern discovery
    Extensible functionality with Jython and R
    Intuitive graphical displays
    Integrated toolbox for pathway analysis and biological contextualization
    Agilent also has Natural language processing-based (NLP) algorithms that are available for application to a body of text, HTML, a PDF, or Medline XML to extract and add interactions to an existing interaction database.
5. Co-pending U.S. application Ser. No. 13/264,843 filed Apr. 14, 2010, the contents of which are hereby incorporated herein by reference, describes methods to specifically detect and differentiate one or more miRNAs in miRNA maturation pathway.

Example 1. Producing 3D Tumor Tissue Models

Tumor spheroids and Tumor histoids (TH/3DH) are produced in either one of the two 3D culture modes: 1. low shear, rotating suspension culture or 2. hanging drop (HD) cultures in 96 or 384 well Perfecta3D™ Hanging Drop Plates. TH are cultured in two stages: a. generation of fibroblast spheroids using normal newborn foreskin fibroblasts, b. addition of tumor cells (various ATCC lines) to the preformed spheroids.

Bioreactor Culture Procedure: (1).

$120.0 \times 10^6$ fibroblasts in 60 ml of culture medium are introduced into the culture chamber and rotated at approximately 6 rpm for five hours during which they form spheroids. (2). Tumor cells in 4 ml medium are added to completely fill the chamber and rotation is continued for the duration of culture (approximately 10 days).

Bioreactor Cultures:

Cancer cells coat and invade the fibroblast core producing extracellular matrix during culture. One 64 ml culture typically yields approximately 600 individual TH particles, each a few tenths of a millimeter in diameter. Histologically, TH closely resemble actual tumor microlesions (illustrated in U.S. Pat. No. 6,998,264, the contents of which are incorporated herein by reference).

Example 2. miRNA and Gene Expression Microarray Analysis

Cells of normal foreskin fibroblast (NF), breast cancer line UACC-893 (UA) and prostate cancer line DU-145 (DU) were cultured in 2D and 3D bioreactor. 2D cultures were harvested at confluence. Cells of 3D spheroids (single cell type) and histoids, with fibroblast core and tumor cells UACC-893 or DU-145 (FIGS. 3b and 3c) were cultured in bioreactor. Spheroids were harvested on day 4 and histoids on day 10 and cryopreserved. For miRNA and gene expression analysis cryopreserved samples were shipped on dry ice to Ambry Genetics, CA, a CLIA service provider.

Total RNA was isolated according to Ambion mirVana miRNA Isolation Kit protocol. RNA quality and concentration was determined on NanoDrop spectrophotometer and bioanalyzer. Labeling reactions were carried out using Agilent miRNA two part Complete Labeling and Hyb Kit (Version 2.1) with 100 ng total RNA input. Samples were placed on human 15K miRNA array V3 with a layout 1 human 8×15K miRNA array V3. The arrays were scanned at 5 µM resolution on Agilent G2565CA high Resolution Scanner. Gene expression analysis was carried out with Agilent Single Color on SurePrint G3 Human 8×60 Microarray.

Example 3. Analysis of miRNA Microarray Data

Figure 2:
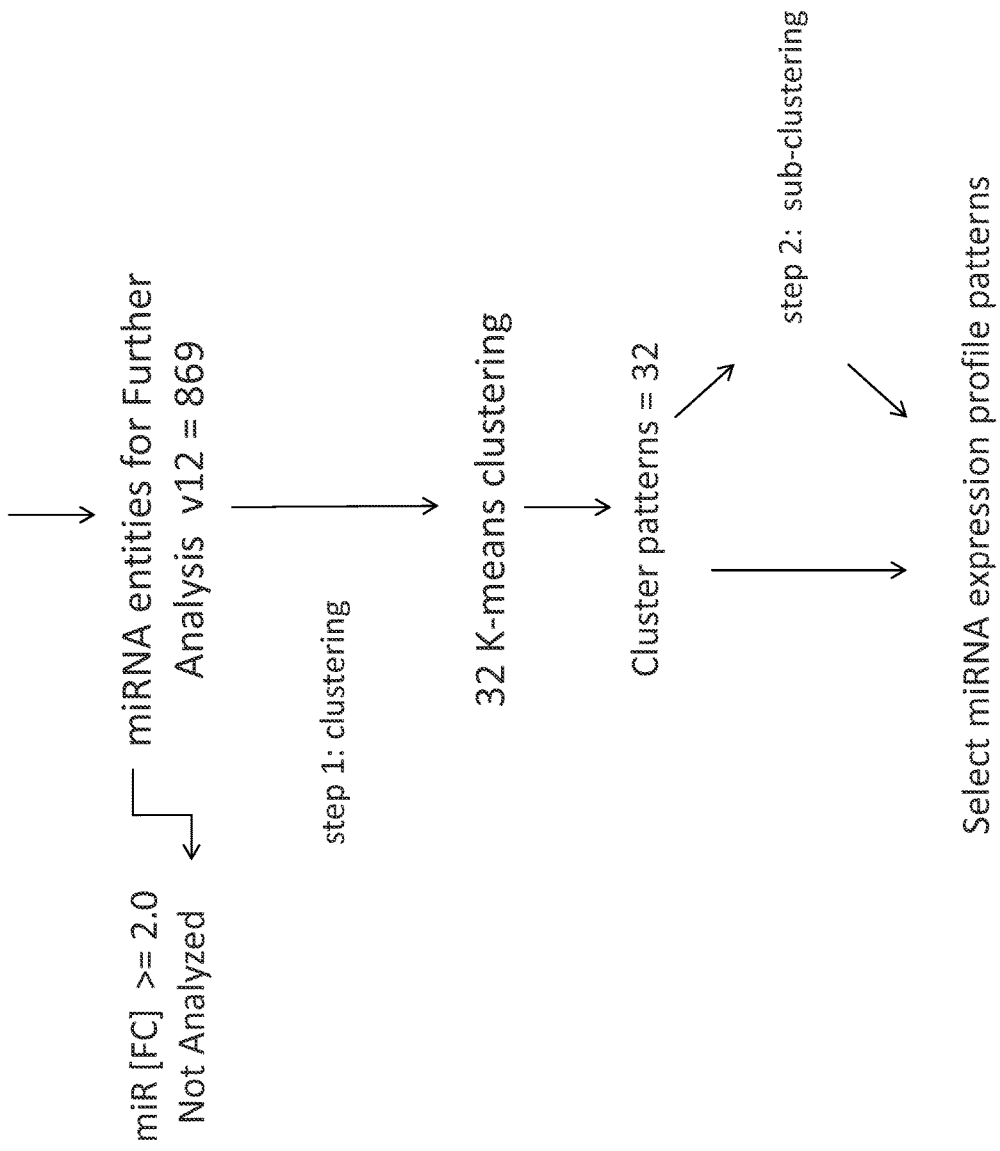
FIG. 2 shows part II_a of the analytical workflow in which the filtered v12 miRNA list was subjected directly to 32 K-means clustering and sub-clustering analysis.
Figure 3:
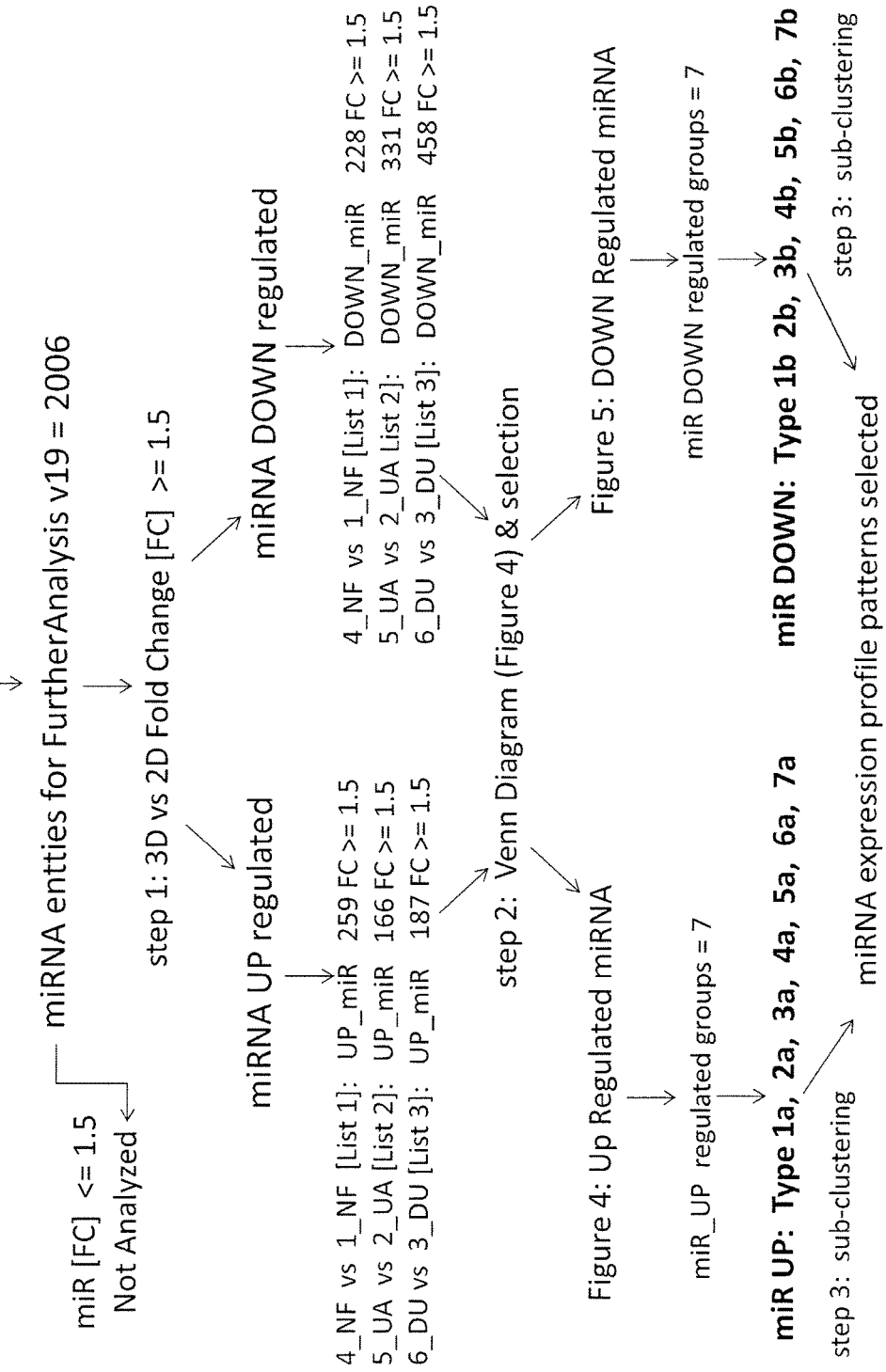
FIG. 3 shows part II_b of the analytical workflow in which the filtered v19 miRNA list was first subjected to pairwise 3D versus 2D fold change [FC>=1.5] analysis for normal (NF), breast tumor (UA) and prostate tumor (DU) samples.
Figure 4:
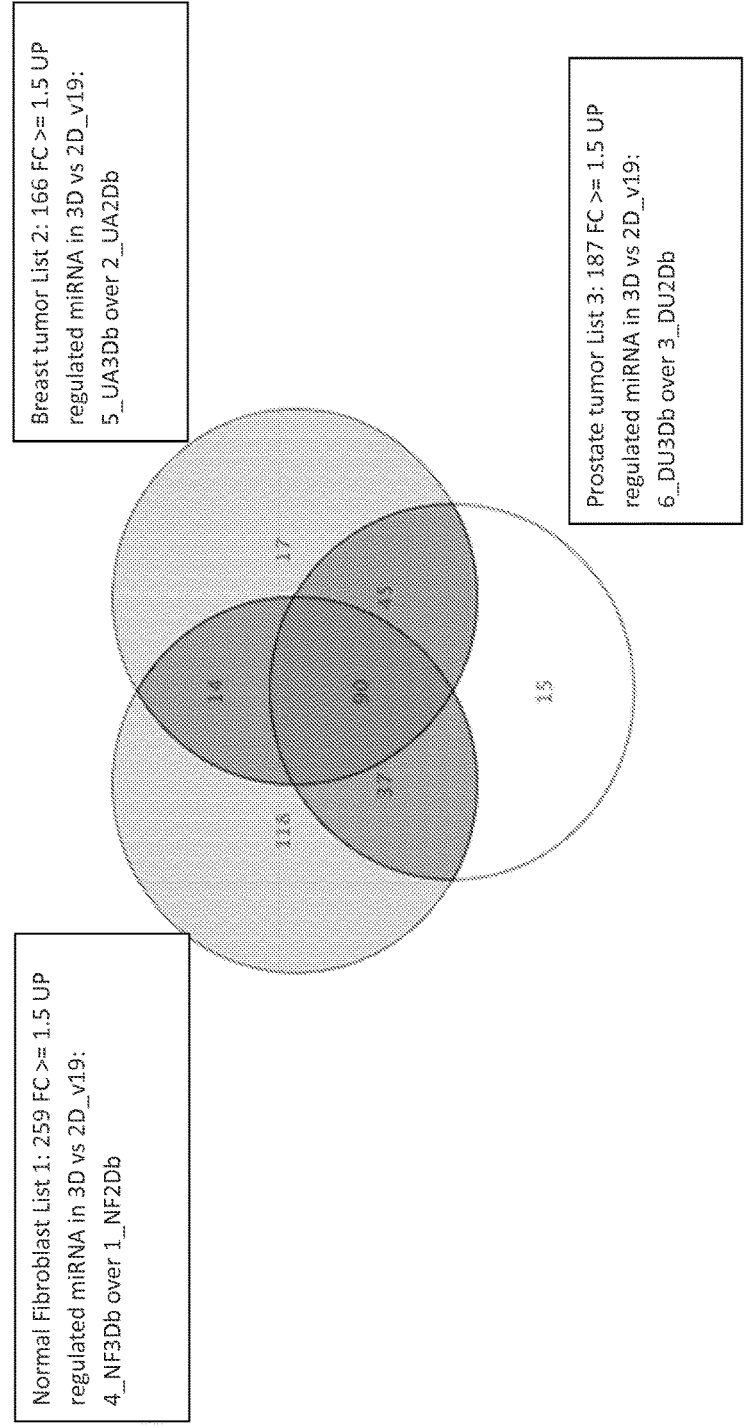
FIG. 4 and FIG. 5 show a three way Venn diagram of the up and down regulated miRNA list obtained in the 3 pairs (FIG. 3) that resulted in 7 up regulated miRNA groups (1a, 2a, 3a, 4a, 5a, 6a, 7a) and 7 down regulated (1b, 2b, 3b, 4b, 5b, 6b, 7b) that were further clustered and sub-clustered, from which miRNA expression profile patterns were selected.
Figure 5:
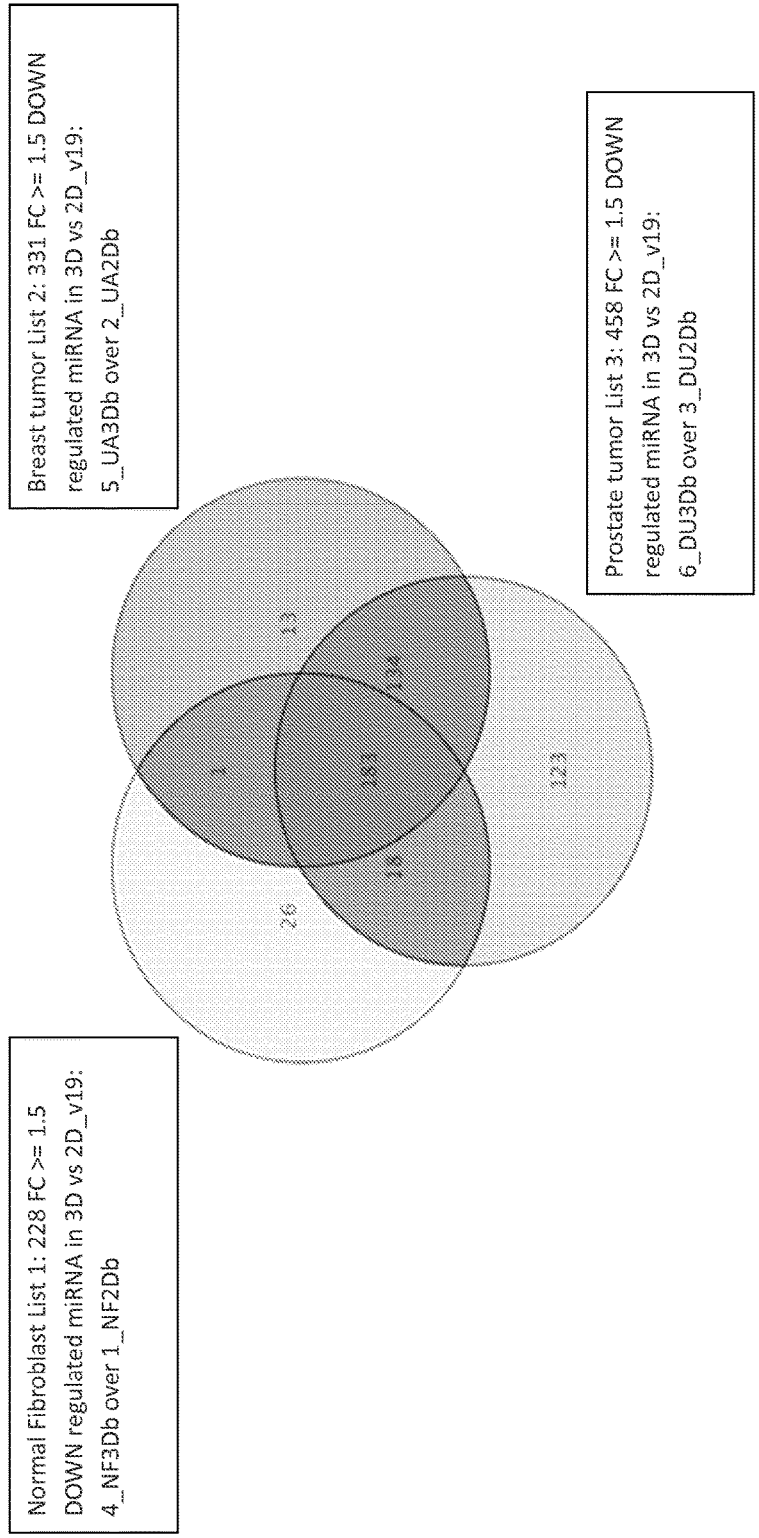

A set of 8 samples was applied to v12 or v19 miRNA microarrays ([1]-NF2D, [4]-NF3D (Normal Fibroblast), [2]-UA2D, [5]-UA3D (breast cancer), [3]-DU2D, [6]-DU3D (prostate cancer), [7]-NFUA3DH, [8]-NFDU3DH, wherein 2D designates monolayer culture, 3D designates 3D spheroid culture and 3DH designates 3D histoid culture). The raw data from (probe signal intensity values) was transformed into log 2 miRNA Gene Signal Intensity Values. Subsequently all miRNA entities across all samples in v12 (984 entities) and v19 (2027 entities) normalized by quantile normalization with no baseline transformation. At the next step All controls and all viral microRNA from normalized data set were filtered with search and Venn diagram functions. After this step: 869 miRNA entities (v12) or 2006 miRNA entities (v19) were taken forward to the next step of analysis (FIG. 1). Subsequently v12 set was subjected to 32 K-means clustering (FIG. 2). The v19 set on the other hand was subjected first to pairwise fold-change [FC>=1.5] analysis (NF3D vs NF2D, UA3D vs UA2D, DU3D vs DU2D) to identify the miRNAs whose expression differed by at least 1.5 fold between the samples in the pair (FIG. 3). This analysis yielded 2 groups of up and down regulated miRNA list for each of the three pairs of normal, breast and prostate tumor 3D and 2D sample sets. A three way Venn diagram analysis was carried out using the up regulated (FIG. 4) and down regulated (FIG. 5) miRNA list of the three pairs, which yielded 7 groups of up regulated miRNA (FIG. 4) and 7 groups of down regulated miRNA (FIG. 5). The number of miRNA in each of the up regulated and down regulated in each of the groups is listed in Table I.

Figure 6:
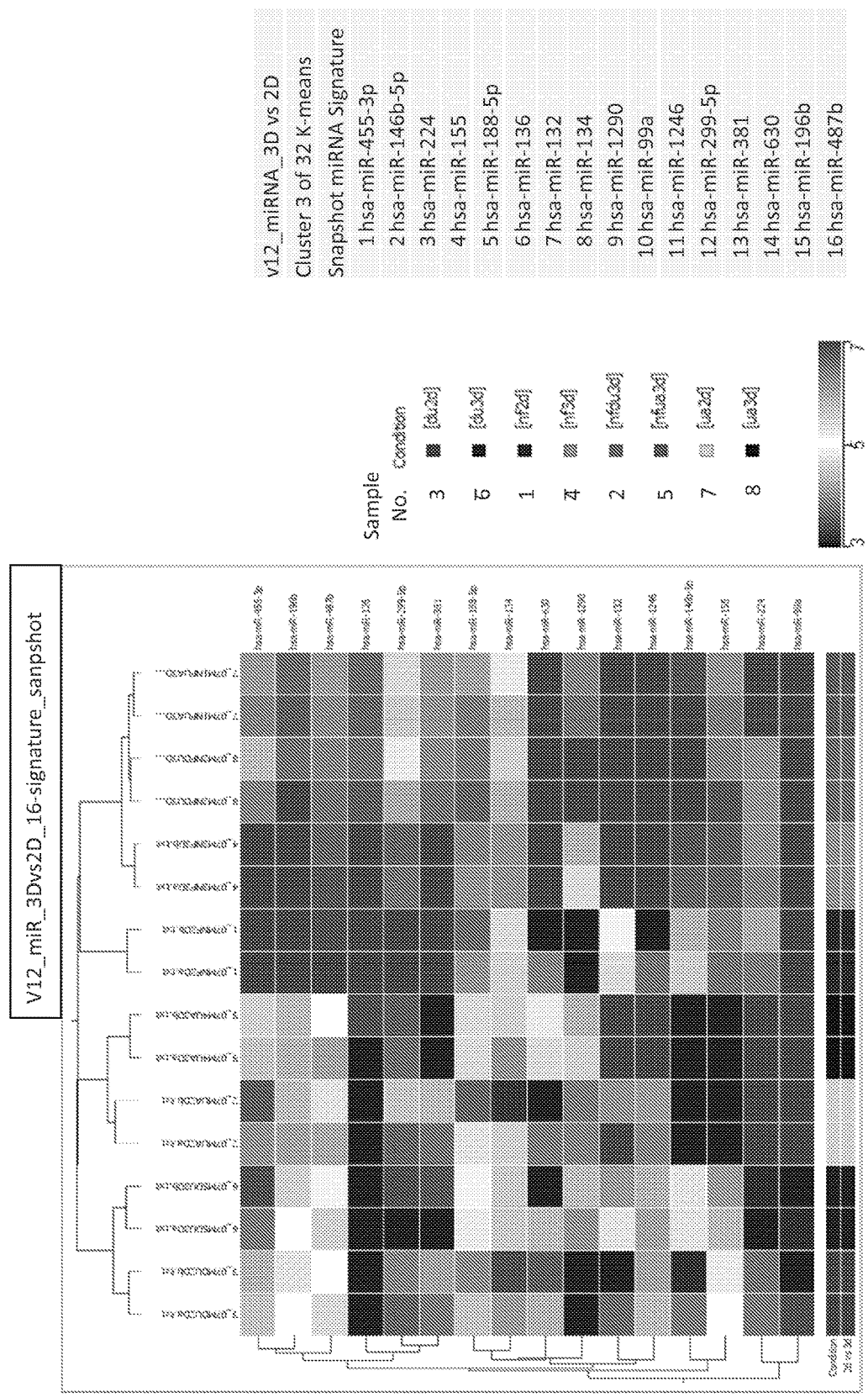
FIG. 6 shows the heat map of the 16 miRNA signature cluster 3-32 of v12 (FIG. 2), obtained through 32 K-clustering analysis of 2D and 3D spheroid and 3D histoid cultures of normal foreskin fibroblasts, breast cancer cells and prostate cancer cells.

Example 4. miRNA Expression Profile: 3D Tissue miRNA Signature 961 miRNA normalized across the eight samples in two replicates in [1-NF2D, 4-NF3D (Normal Fibroblast), 2-UA2D, 5-UA3D (breast cancer), 3-DU2D, 6-DU3D (prostate cancer), 7-NFUA3DH (breast cancer histoid), 8-NFDU3DH (prostate cancer histoid)] samples were subjected to two methods of enrichment (FIG. 1): 1. 32 K-means clustering and 2. 3D vs 2D>=2.0 log fold change analyses. With the v12 miRNA entities only the 32 K-means clustering method was carried forward (FIG. 2). 32K-means clustering. 32 K-means clustering analysis was carried to cluster 961 miRNA normalized across the eight samples in two replicates. The samples analyzed were [1]-NF2D, [4]-NF3D (Normal Fibroblast), [2]-UA2D, [5]-UA3D (breast cancer), [3]-DU2D, [6]-DU3D (prostate cancer), [7]-NFUA3DH (breast cancer histoid), [8]-NFDU3DH (prostate cancer histoid). The parameters used for the miRNA analysis were to differentiate 3D cells vs 2D, spheroids vs histoid and that of normal NF vs breast and prostate cancer. Cluster number 3 of 32 K-means (cluster 3-32) met the criteria used for differentiating between the different parameters. The 3-32 cluster profiled a panel of 16 miRNAs and was identified as signature miRNA for the criteria used above. Hierarchical clustering profile of the 16 signature miRNA Signature-1 (FIG. 6) differentiates 3D cells from 2D, normal and cancer spheroids from histoids in the sample set profiled.

Core 10 miRNA profile distinguish 3D from 2D in each of the normal and cancer samples. 3D shift from 2D reflected tissue specific changes in signature-1 miRNA profile in normal (NF) and cancer (UA, DU) samples. Conserved targets of signature-1 miRNA from TargetScan database (>80 context percentile score) in gene ontology (GO) analysis identified chromatin modification as one of the significant (7.101E-8) biological process in 3D models, including also DNA binding (6.926E-13), regulation of gene expression (3.6E-24) and transcription regulator activity (6.904E-19).

Of the 34515 non-coding and coding gene expressions profiled, 83 histone and 90 histone modifier GE entities were recovered. Histones GE profile, especially HIST-1 cluster group differentiates breast (UA) and prostate (DU) cancer samples from normal fibroblast (NF). Histone modifiers GE profile differentiate breast cancer (UA) from prostate cancer (DU) and normal (NF). Specific histone and histone modifier genes shown with miRNA overlay are possible putative targets of 13 miRNAs that signature 3D models shift from 2D in normal and cancer cell.

Figure 7:
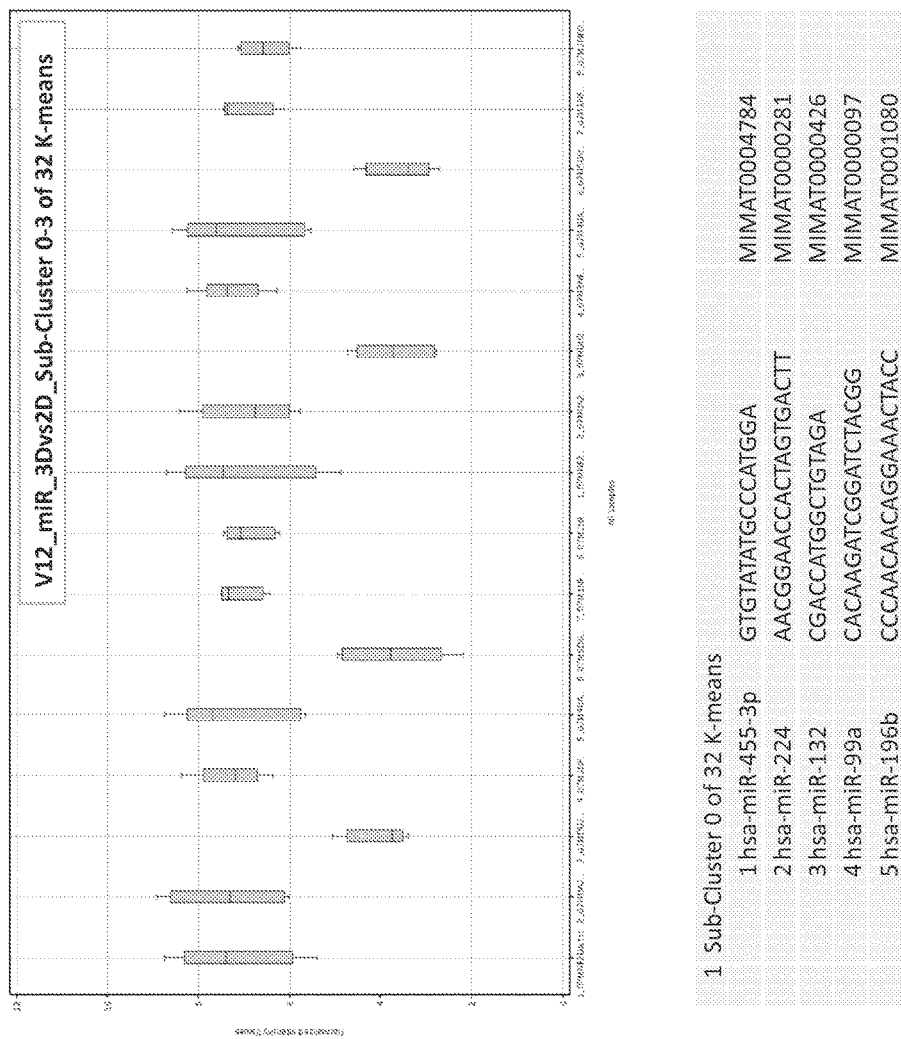
FIG. 7, FIG. 8 and FIG. 9 show the 3 sub-clusters of (v12) miRNA cluster 3-32 K-means yielding 3 distinct profiles of 5 miRNAs in sub-cluster 0-3-32.
Figure 8:
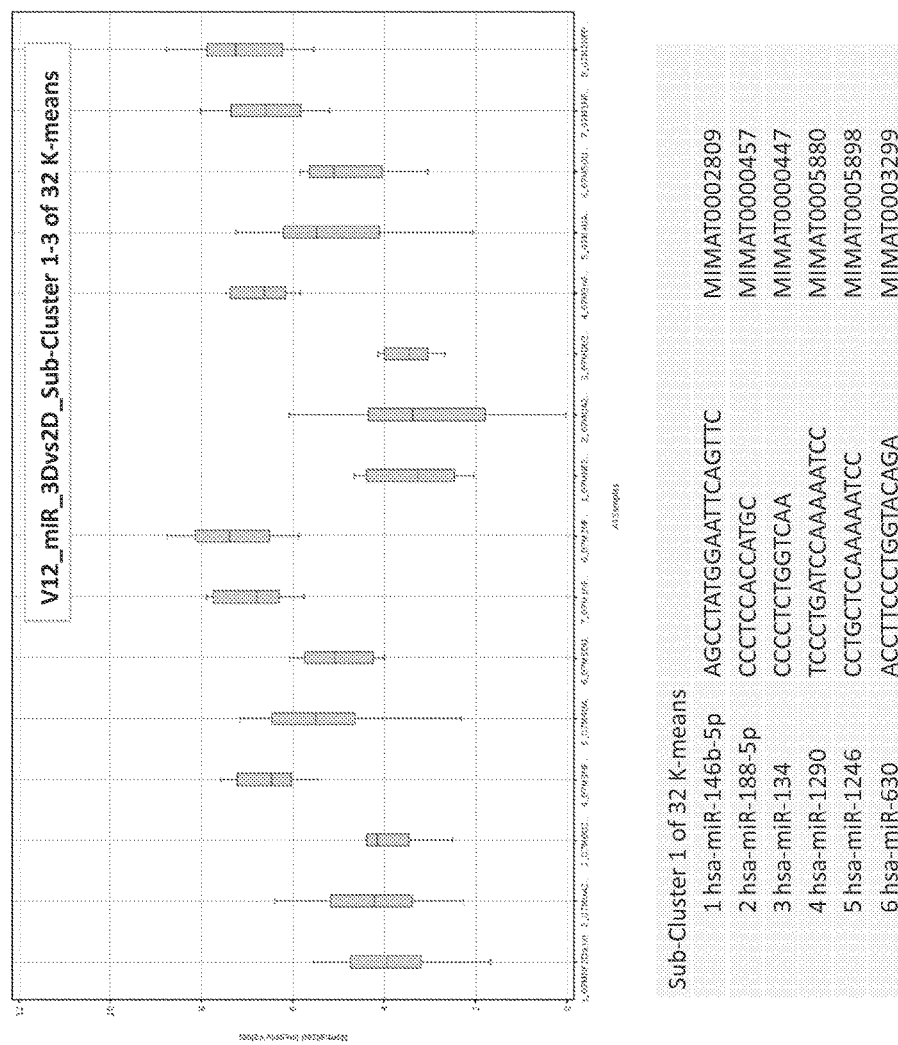
Figure 9:
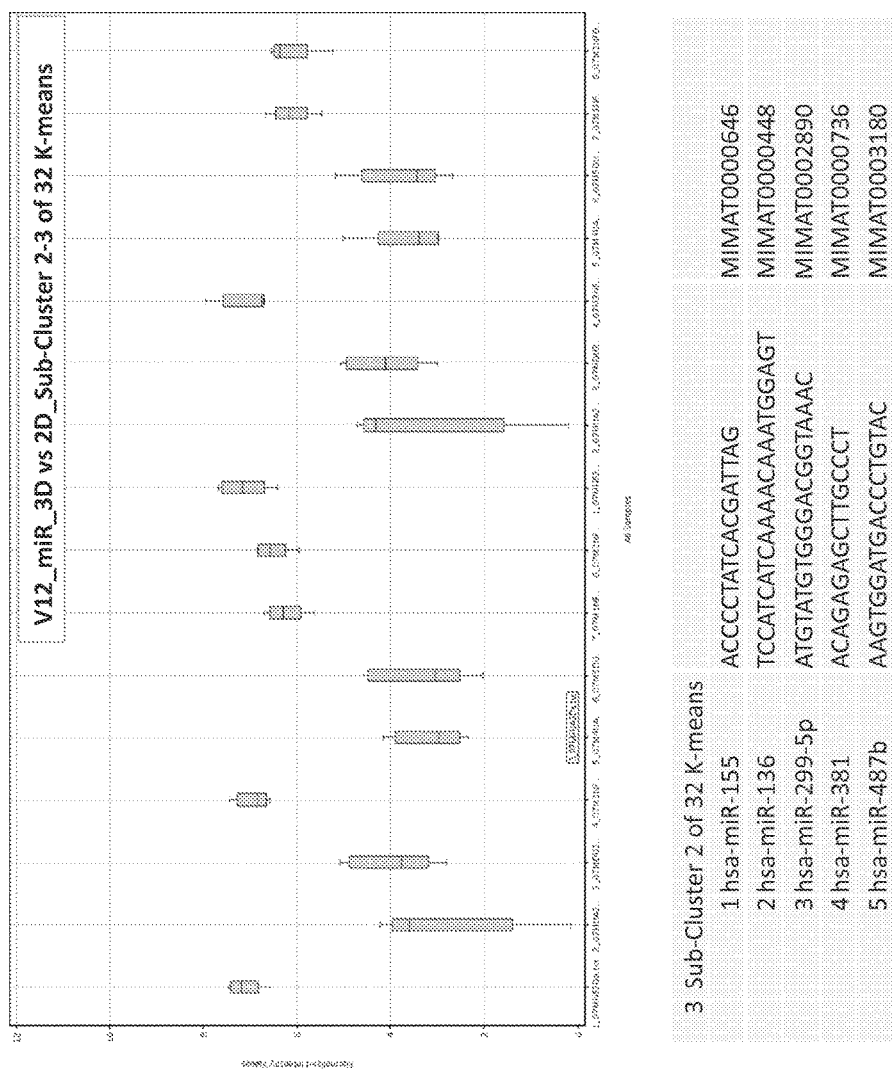

The 16 Signature-1 miRNAs were also further sub-clustered which yielded 3 distinct profiles (FIG. 7, 8, 9): 5 miRNAs in sub-cluster 0-3-32 K-means differentiated normal and breast cancer from prostate cancer and was similar both in 3D and 2D cultures; 6 miRNAs in sub-cluster 1-3-32 K-means differentiated 3Ds from 2Ds and histoids from spheroids; and 5 miRNAs in sub-cluster 2-3-32 K-means differentiated cancer from the normal.

Example 5. Identification of miRNA Signature and Integrated Gene Expression Network with GO Function in 3D Multicellular Micro-Tissue Models Versus Monolayer Cells Agilent GeneSpring (GS) GX 11.0.1 platform was used for microarray data analysis. miRNA and expression profiles (Example 4) and gene expression profiles (Example 2) were analyzed after quantile normalization. Signature miRNA gene targets were identified using TargetScan database 5.0 and 6.0 (TS) with miRNA seed recognition sequence at context score percentile >80 percent for conserved targets. The in silico miRNA gene targets identified from TargetScan was translated to find expressed genes from gene expression profiles of the samples. Using the gene ID and GO terms the functions of the gene targets involved were identified and a miRNA integrated expressed gene target list was produced. GO functions with significantly high p-value and unique to a miRNA cluster was identified and gene interaction network was created using NLP. The target gene interaction network was overlaid with associated miRNA in a cluster group.

Figure 10:
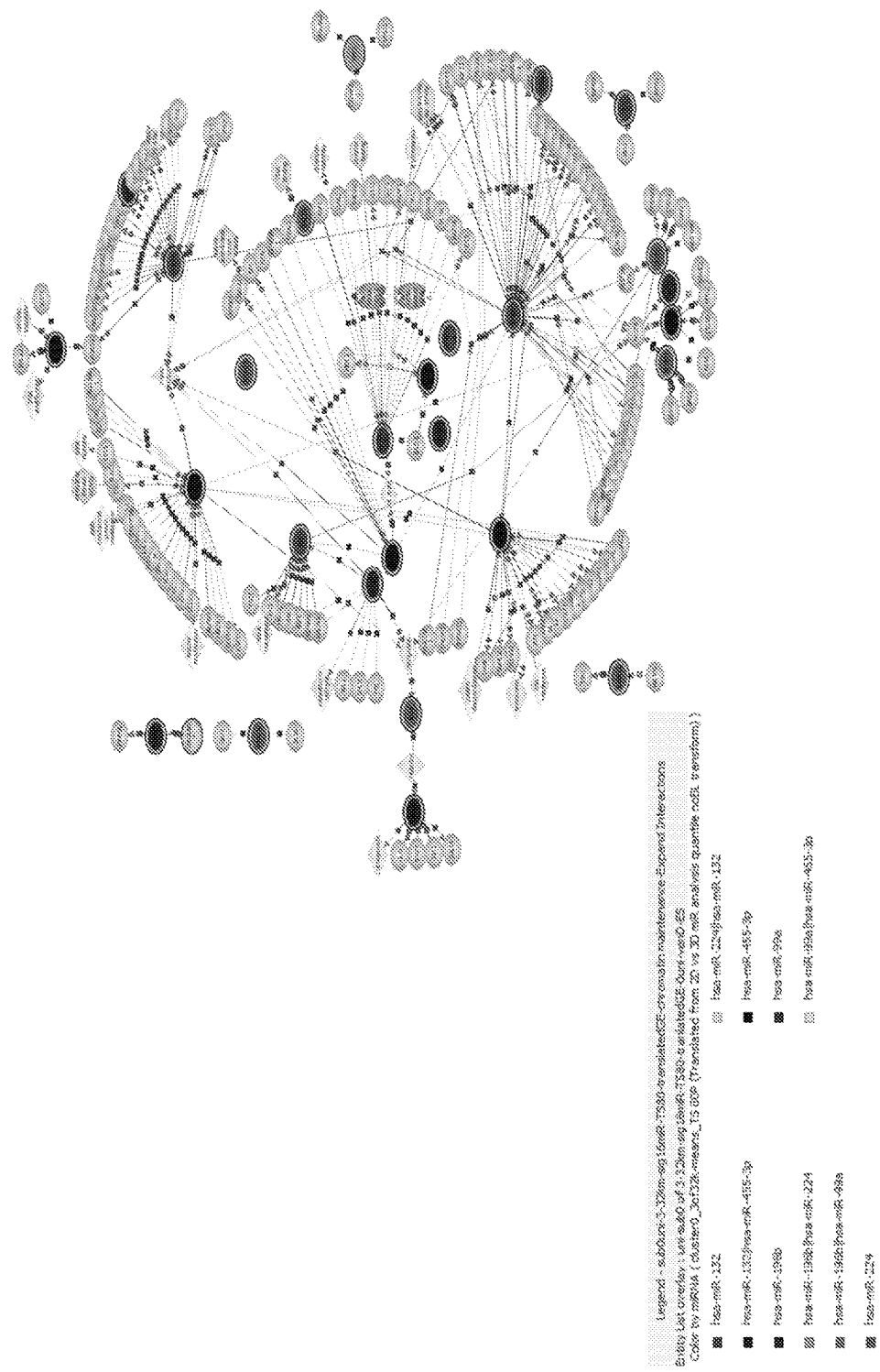
FIG. 10 shows v12 miRNAs of 0-3-32 cluster integrated with expressed gene targets and network in chromatin architecture modifications.
Figure 11:
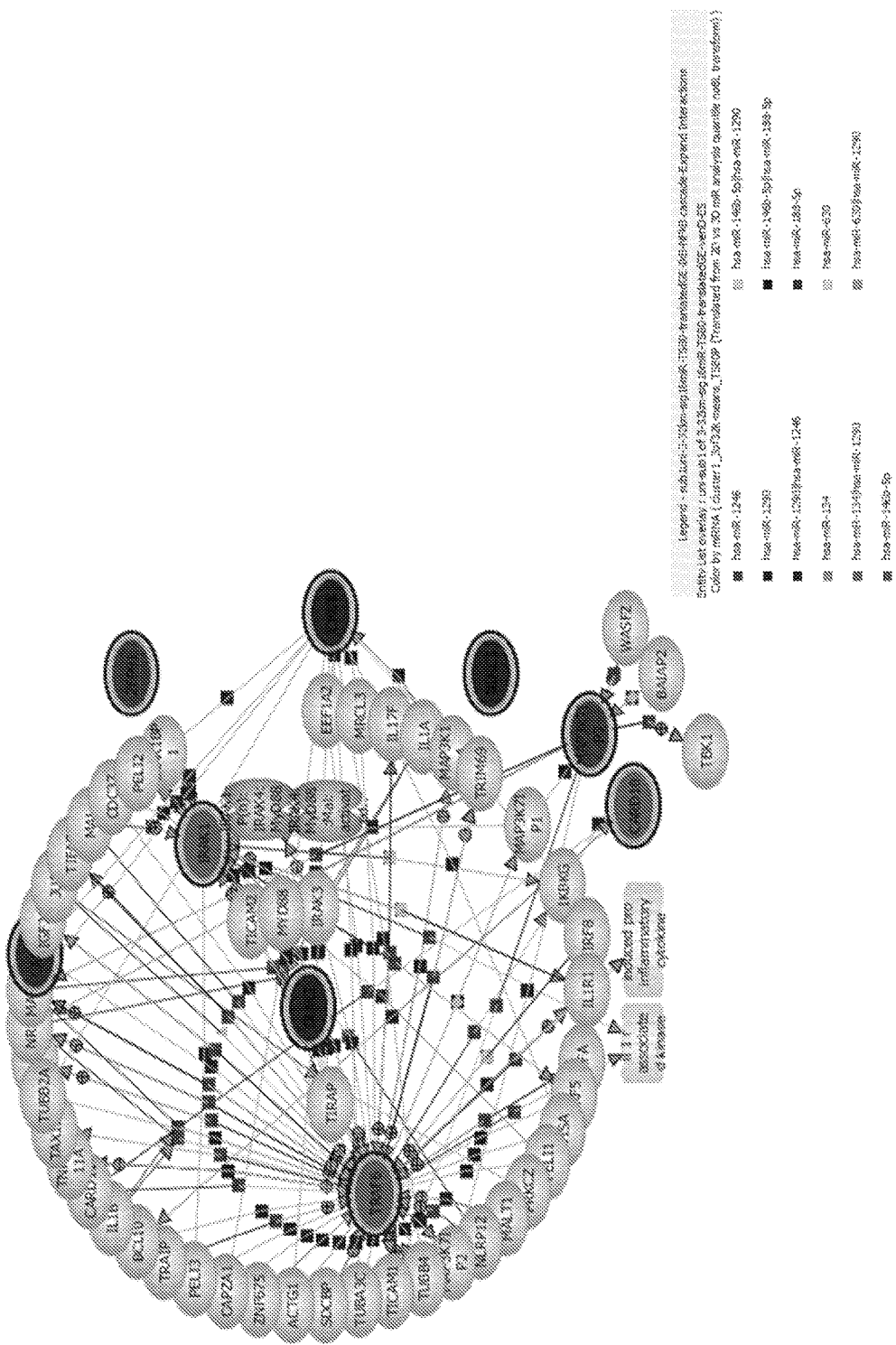
FIG. 11 shows v12 miRNAs of 1-3-32 cluster integrated with expressed gene targets and network in NF-kB cascade.
Figure 12:
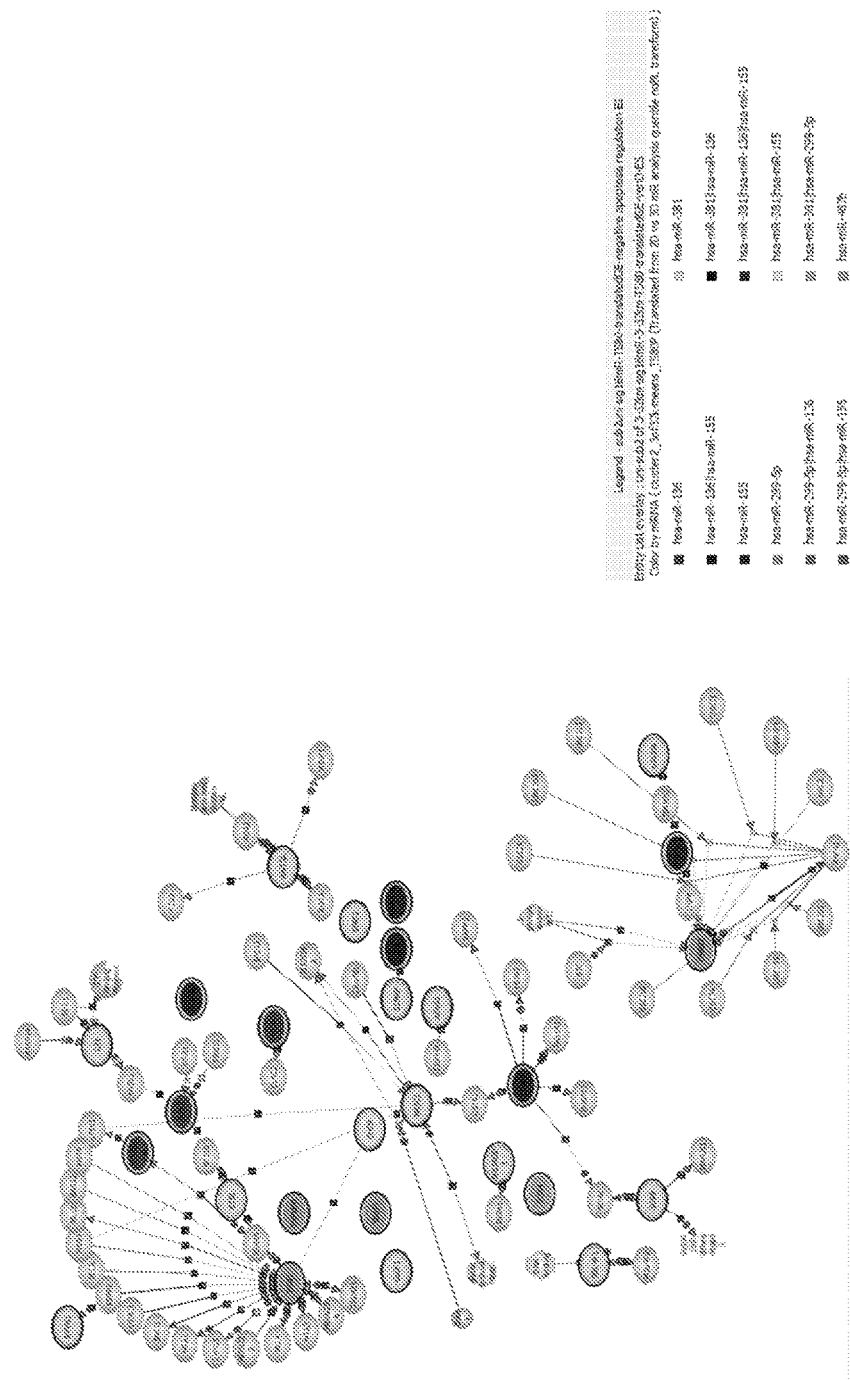
FIG. 12 shows v12 miRNAs of 2-3-32 cluster integrated with expressed gene targets and network in -ve apoptosis.
Figure 13:
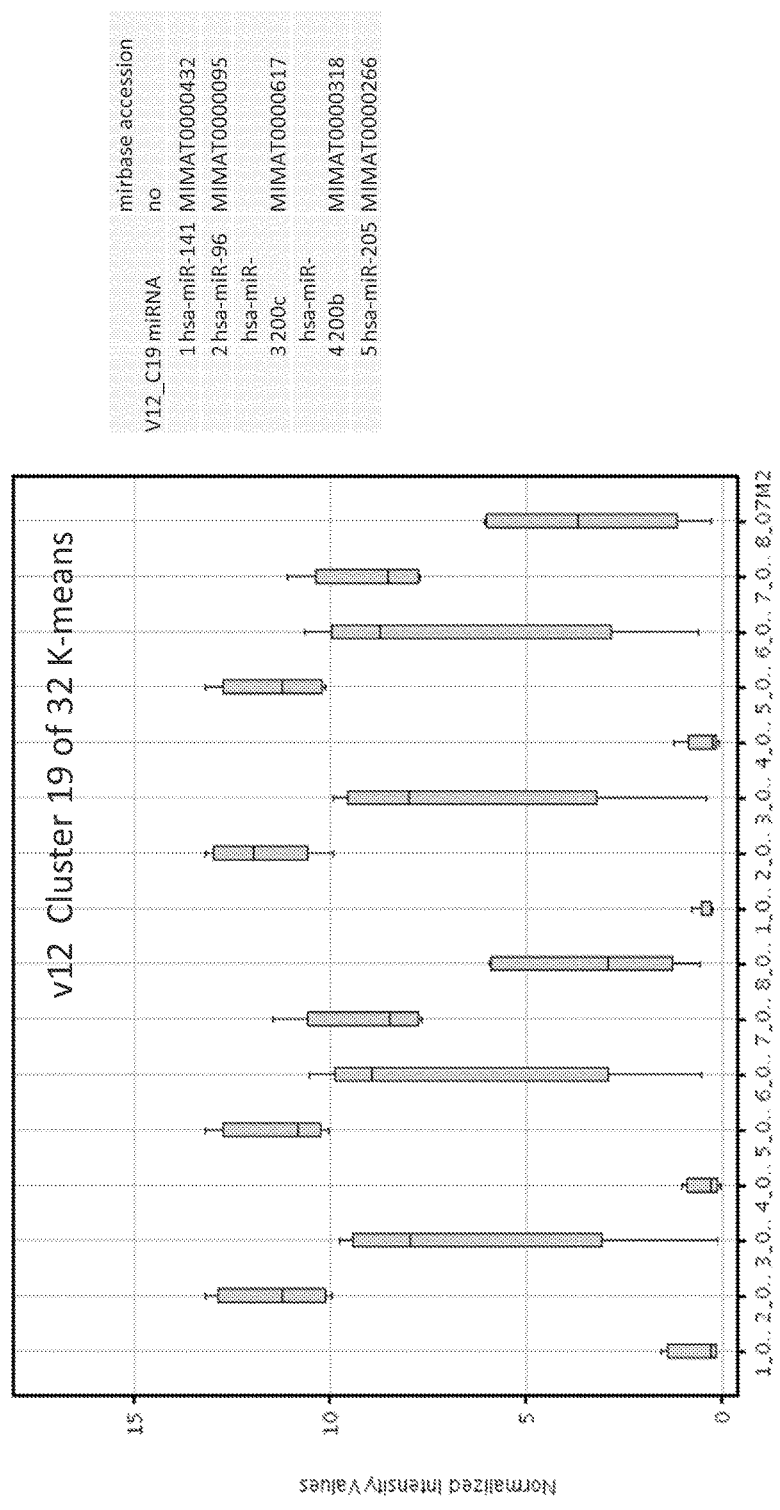
FIG. 13 and FIG. 14 show v12 miRNAs of 19-32 K-means cluster that consists of 5 miRNAs in 19-32 cluster and 7 miRNAs in 27-32 K-means cluster.
Figure 14:
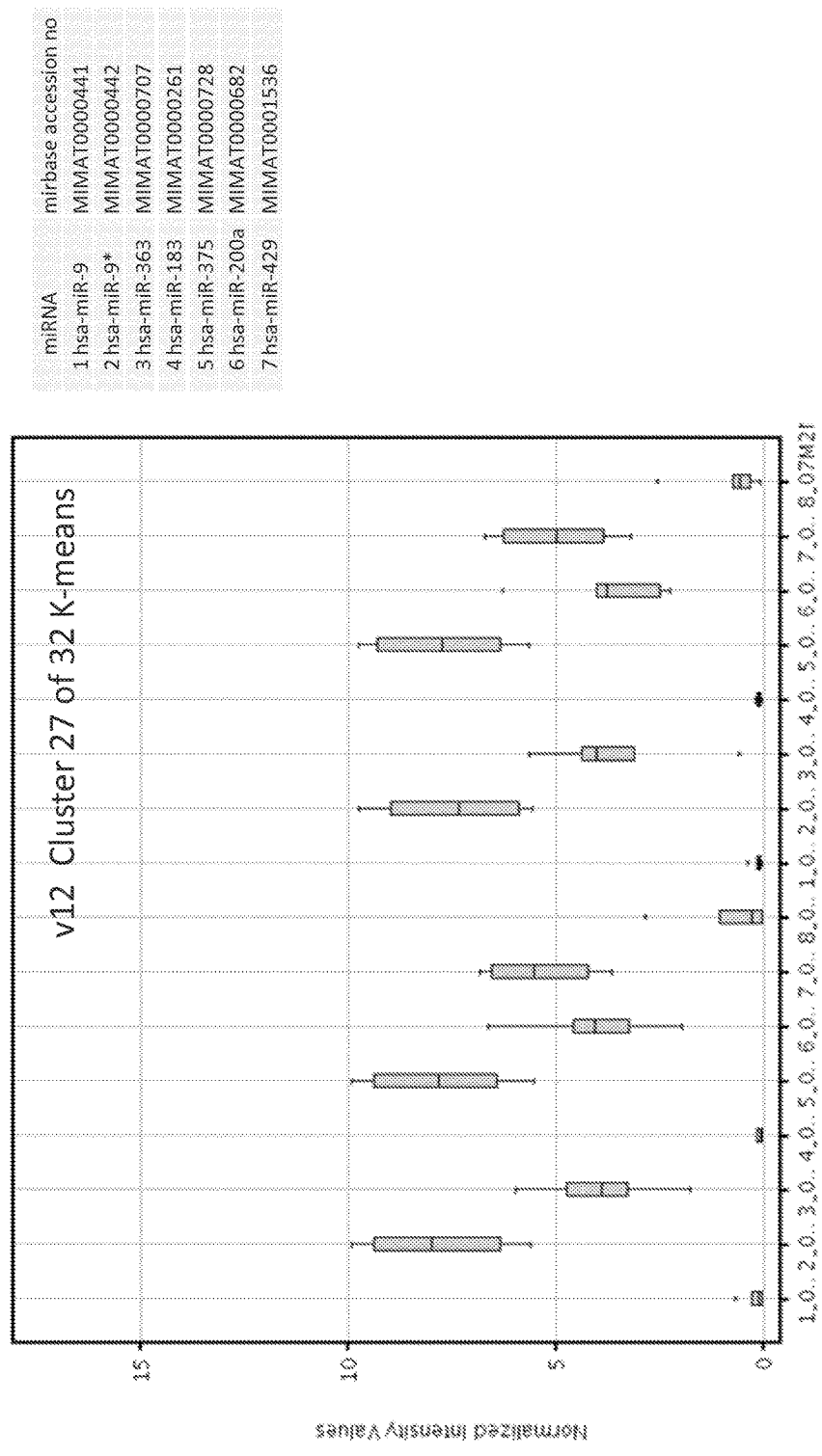
Figure 15:
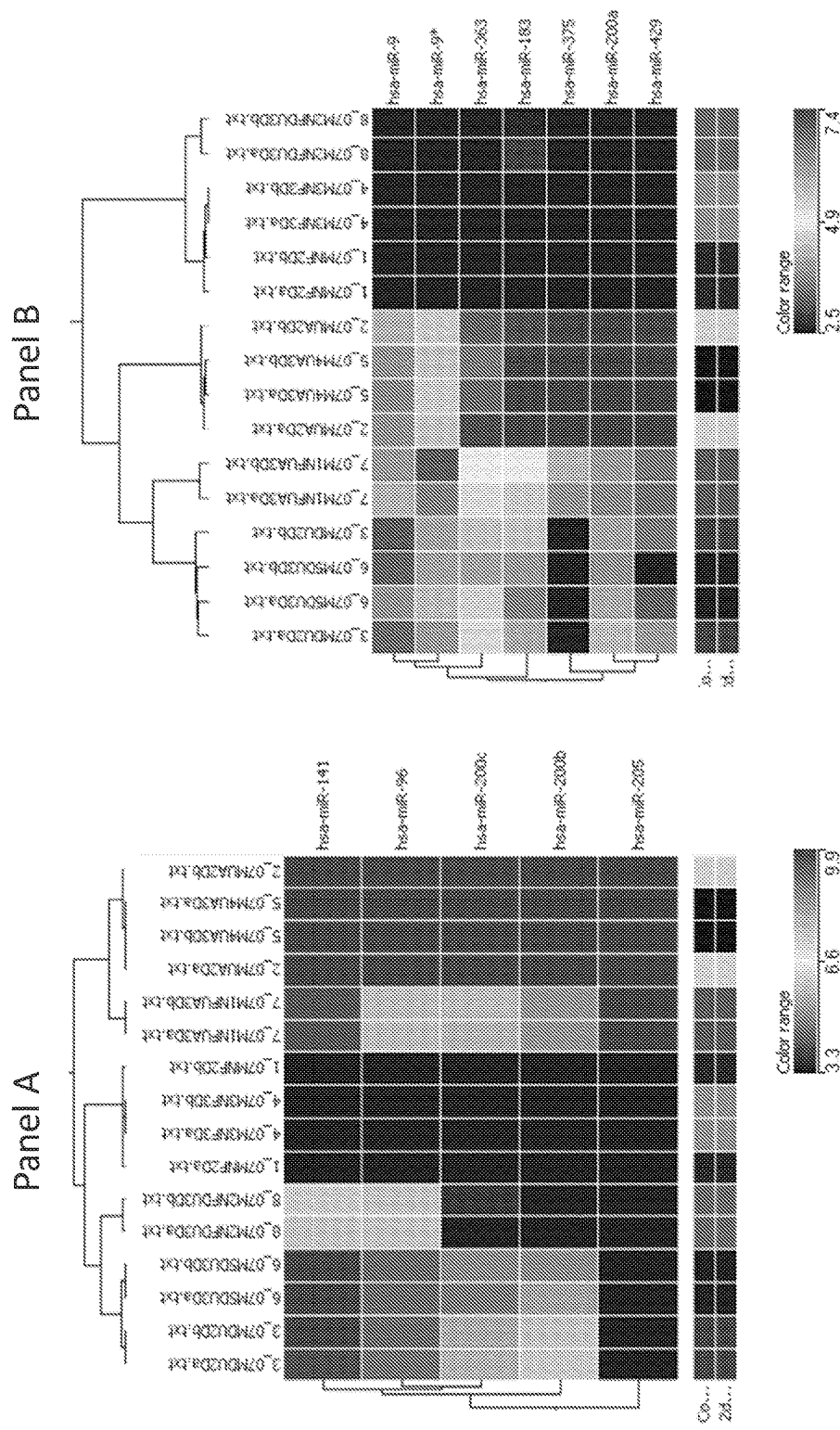
FIG. 15 Panel A and Panel B show heat maps of miRNAs in cluster 19-32 and 27-32.
Figure 16:
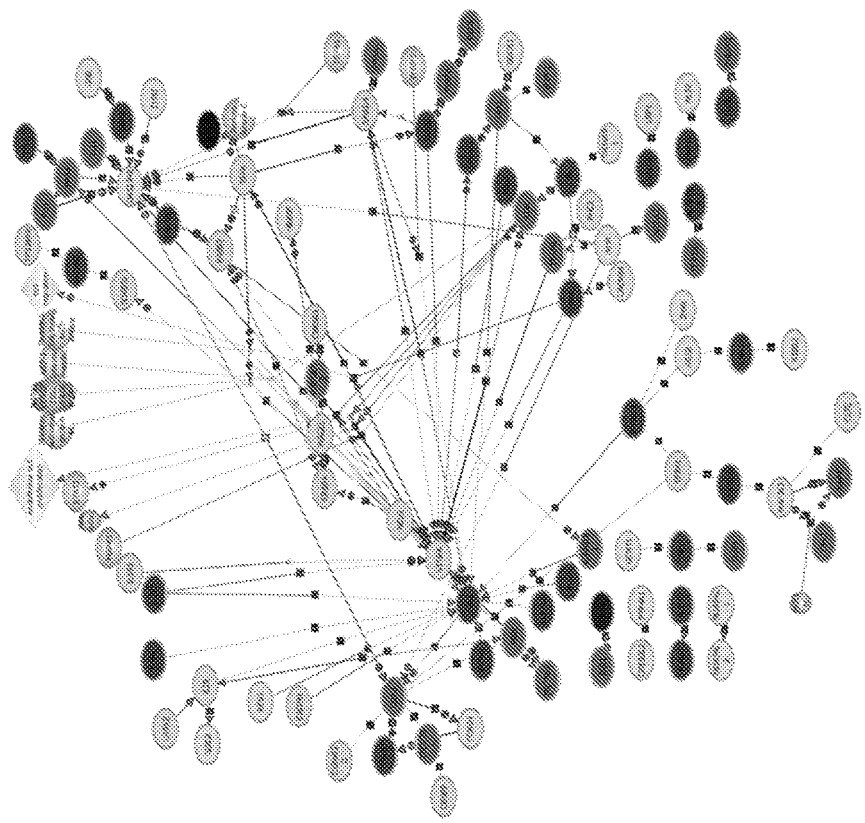
FIG. 16 shows miRNAs of 19-32 and 27-32 K-means clusters integrated with expressed gene targets and network in blood vessel formation.

Example 6. mRNA Expression Profiles: miRNA to mRNA Target Entity(s) Integration and Relationship From GO analysis (p-value <0.05), the miRNA related target genes involved in cellular processes and network relationships that is unique to each sub-cluster was identified: 1. miRNA sub-cluster 0-3-32 to genes expressed in chromatin architecture maintenance and modifications (FIG. 10 p-value 1.396E-5); 2. miRNA sub-cluster 1-3-32 to gene expressed genes in NF kappaB inflammatory response cascade (p-value 5.602E-6) (FIG. 11); 3. miRNA sub-cluster 2-3-32 to expressed gene in negative regulation of apoptosis (p value 1.583E-5) (FIG. 12).

Example 7. Cluster Types of miRNA Signature Profile miRNA groups identified using human miRNA microarray V19 data analysis (FIG. 3) narrated in Example 3 which was segregated into 7 pairs Venn diagram groups of up and down regulated miRNAs is listed in Table I. Each one of the group was further subjected to K-means clustering (the number of K-means chosen depended upon the number of entities in each group) and sub-clustering analysis in order to identify miRNAs that are specific to a particular expression pattern. The parameters used to recognize and differentiate miRNA expression pattern and types were log 2 expression values with FC>=1.5 and furthermore the extent of up and down regulated fold change of a cluster of miRNA generated across all of the samples and graphed in a box whisker plot. The expression profile and pattern of a set of miRNA in a cluster or sub-cluster in a specific Venn group and cluster type was given an alphanumeric label, and are listed below Table I.

TABLE I

Three way Venn diagram segregated groups of up and down regulated miRNA in the three condition pairs Normal 3D_NF vs 2D_NF, breast tumor 3D_UA vs 2D_UA and prostate tumor 3D_DU vs 2D_DU

| VennD Group | Presence | v19 3D vs 2D FC >=1.5 | | | miRNA entities | |
|---|---|---|---|---|---|---|
| | | NF | UA | DU | Type 1: UP | Type 1: DOWN |
| 1 | common | NF | UA | DU | 90 | 183 |
| 2 | common | NF | UA | x | 14 | 1 |
| 3 | common | NF | x | DU | 37 | 18 |
| 4 | common | x | UA | DU | 45 | 134 |
| 5 | Unique | NF | x | x | 118 | 26 |
| 6 | Unique | x | UA | x | 17 | 13 |
| 7 | Unique | x | x | DU | 15 | 123 | x is Fold Change <=1.5

Type 1a or first type;
Type 1b or second type;
Type 2a or third type;
Type 2b or fourth type
Type 3a or fifth type;
Type 3b or sixth type;
Type 4a or seventh type;
Type 4b or eighth type
Type 5a or ninth type;
Type 5b or tenth type;
Type 6a or eleventh type;
Type 6b or twelfth type
Type 7a or thirteenth type;
Type 7b or fourteenth type;

TABLE II

Type 1a or "first type" miRNAs that are down regulated or not detected when the tumor cells and normal cells are grown in monolayer culture and is up regulated and significant as a fold change of at least 1.5 when the tumor cells and normal cells are grown in multicellular culture

| | miRNA Type 1a-1_1 | mirbase accession No |
|---|---|---|
| 1 | hsa-miR-1304-3p | MIMAT0022720 |
| 2 | hsa-miR-191-3p | MIMAT0001618 |
| 3 | hsa-miR-371b-5p | MIMAT0019892 |
| 4 | hsa-miR-4291 | MIMAT0016922 |
| 5 | hsa-miR-4532 | MIMAT0019071 |
| 6 | hsa-miR-4634 | MIMAT0019691 |
| 7 | hsa-miR-4788 | MIMAT0019958 |
| 8 | hsa-miR-6126 | MIMAT0024599 |
| 9 | hsa-miR-642b-3p | MIMAT0018444 |
| 10 | hsa-miR-663a | MIMAT0003326 |

TABLE III

Type 1b or "second type" miRNAs that are up regulated when the tumor cells and normal cells are grown in monolayer cells and is down regulated and significant as a fold change of at least 1.5 when the tumor cells and the normal cells are grown in multicellular culture

| | v19_miR_Type 1b-2 | mirbase accession No |
|---|---|---|
| 1 | hsa-miR-103a-2-5p | MIMAT0009196 |
| 2 | hsa-miR-130a-5p | MIMAT0004593 |
| 3 | hsa-miR-1343 | MIMAT0019776 |
| 4 | hsa-miR-15a-3p | MIMAT0004488 |
| 5 | hsa-miR-1913 | MIMAT0007888 |
| 6 | hsa-miR-196b-3p | MIMAT0009201 |
| 7 | hsa-miR-1976 | MIMAT0009451 |
| 8 | hsa-miR-3619-3p | MIMAT0019219 |
| 9 | hsa-miR-3622a-3p | MIMAT0018004 |
| 10 | hsa-miR-4308 | MIMAT0016861 |
| 11 | hsa-miR-4722-3p | MIMAT0019837 |
| 12 | hsa-miR-4756-5p | MIMAT0019899 |
| 13 | hsa-miR-642b-5p | MIMAT0022736 |
| 14 | hsa-miR-6510-3p | MIMAT0025477 |

TABLE IV

Type 2a or "third type" miRNAs that are down regulated when the tumor cells and normal cells are grown in monolayer cells and is up regulated and significant as a fold change of at least 1.5 in the normal cells, but not in breast tumor cells or prostate tumor cells, when grown in multicellular culture

| | miR_Type 2a-2 | mirbase accession No |
|---|---|---|
| 1 | hsa-miR-129-1-3p | MIMAT0004548 |
| 2 | hsa-miR-1290 | MIMAT0005880 |
| 3 | hsa-miR-146b-5p | MIMAT0002809 |
| 4 | hsa-miR-151b | MIMAT0010214 |
| 5 | hsa-miR-154-5p | MIMAT0000452 |
| 6 | hsa-miR-18b-3p | MIMAT0004751 |
| 7 | hsa-miR-19a-3p | MIMAT0000073 |
| 8 | hsa-miR-337-5p | MIMAT0004695 |
| 9 | hsa-miR-3685 | MIMAT0018113 |

TABLE IV-continued

Type 2a or "third type" miRNAs that are down regulated when the tumor cells and normal cells are grown in monolayer cells and is up regulated and significant as a fold change of at least 1.5 in the normal cells, but not in breast tumor cells or prostate tumor cells, when grown in multicellular culture

|    | miR_Type 2a-2   | mirbase accession No |
|----|-----------------|----------------------|
| 10 | hsa-miR-602     | MIMAT0003270         |
| 11 | hsa-miR-625-3p  | MIMAT0004808         |
| 12 | hsa-miR-6722-3p | MIMAT0025854         |
| 13 | hsa-miR-98-3p   | MIMAT0022842         |

TABLE V

Type 2b or "fourth type" miRNAs that are up regulated when the tumor cells and the normal cells are grown in monolayer cells and is down regulated and significant as a fold change of at least 1.5 in the normal cells, but not the breast tumor cells or prostate tumor cells, when grown in multicellular culture.

| C14of16 | miR_Type 2b-1     | mirbase accession No |
|---------|-------------------|----------------------|
| 1       | hsa-let-7d-3p     | MIMAT0004484         |
| 2       | hsa-miR-1255b-2-3p| MIMAT0022725         |
| 3       | hsa-miR-300       | MIMAT0004903         |
| 4       | hsa-miR-33a-3p    | MIMAT0004506         |
| 5       | hsa-miR-3927-5p   | MIMAT0022970         |
| 6       | hsa-miR-4474-5p   | MIMAT0019234         |
| 7       | hsa-miR-4493      | MIMAT0019028         |
| 8       | hsa-miR-5088      | MIMAT0021080         |
| 9       | hsa-miR-5090      | MIMAT0021082         |
| 10      | hsa-miR-539-5p    | MIMAT0003163         |
| 11      | hsa-miR-609       | MIMAT0003277         |
| 12      | hsa-miR-640       | MIMAT0003310         |
| 13      | hsa-miR-6500-5p   | MIMAT0025454         |
| 14      | hsa-miR-765       | MIMAT0003945         |

TABLE VI

Type 5a or "ninth type" miRNAs that are down regulated when the tumor cells and the normal cells are grown in monolayer cells and is up regulated and significant as a fold change of at least 1.5 in the normal cells and breast tumor cells, but not the prostate tumor cells, when grown in multicellular culture.

| V19_C6 | miR_Type 5a     | mirbase accession No |
|--------|-----------------|----------------------|
| 1      | hsa-miR-1227-5p | MIMAT0022941         |
| 2      | hsa-miR-125a-3p | MIMAT0004602         |
| 3      | hsa-miR-132-3p  | MIMAT0000426         |
| 4      | hsa-miR-196a-5p | MIMAT0000226         |
| 5      | hsa-miR-572     | MIMAT0003237         |
| 6      | hsa-miR-99a-5p  | MIMAT0000097         |
| 7      | hsa-miR-99b-5p  | MIMAT0000689         |

TABLE VII

Type 6a or "eleventh type" miRNAs that are down regulated when the tumor cells and the normal cells are grown in monolayer cells and is up regulated and significant as a fold change of at least 1.5 in the normal cells and the prostate tumor cells, but not the breast tumor cells, when grown in multicellular culture;

| v19_C 12 | UP_miR_Type 6a-1 | mirbase accession No |
|----------|------------------|----------------------|
| 1        | hsa-miR-2116-3p  | MIMAT0011161         |
| 2        | hsa-miR-30e-5p   | MIMAT0000692         |
| 3        | hsa-miR-31-3p    | MIMAT0004504         |
| 4        | hsa-miR-3676-3p  | MIMAT0018100         |
| 5        | hsa-miR-4270     | MIMAT0016900         |
| 6        | hsa-miR-4310     | MIMAT0016862         |

TABLE VII-continued

Type 6a or "eleventh type" miRNAs that are down regulated when the tumor cells and the normal cells are grown in monolayer cells and is up regulated and significant as a fold change of at least 1.5 in the normal cells and the prostate tumor cells, but not the breast tumor cells, when grown in multicellular culture;

| v19_C 12 | UP_miR_Type 6a-1 | mirbase accession No |
|----------|------------------|----------------------|
| 7        | hsa-miR-4731-3p  | MIMAT0019854         |
| 8        | hsa-miR-4745-5p  | MIMAT0019878         |
| 9        | hsa-miR-5195-3p  | MIMAT0021127         |
| 10       | hsa-miR-6723-5p  | MIMAT0025855         |

TABLE VIII

Type 7a or "thirteenth type" miRNAs that are down regulated when the tumor cells and the normal cells are grown in monolayer cells and is up regulated and significant as a fold change of at least 1.5 in the breast and the prostate tumor cells, but not the normal cells, when grown in multicellular culture.

| V19_C11ofC16 | miRNA_Type-7a-1 | mirbase accession No |
|--------------|-----------------|----------------------|
| 1            | hsa-miR-183-5p  | MIMAT0000261         |
| 2            | hsa-miR-378a-3p | MIMAT0000732         |
| 3            | hsa-miR-4299    | MIMAT0016851         |
| 4            | hsa-miR-96-5p   | MIMAT0000095         |

TABLE IX

Type 7a_sim-1 or "thirteenth type-sim1" v12 miRNAs that are down regulated in normal cells and up regulated in breast and prostate tumor either grown in monolayer culture or when grown in multicellular culture.

| v12_C19 | miRNA_Type-7a-0_1 | mirbase accession no |
|---------|-------------------|----------------------|
| 1       | hsa-miR-141       | MIMAT0000432         |
| 2       | hsa-miR-96        | MIMAT0000095         |
| 3       | hsa-miR-200c      | MIMAT0000617         |
| 4       | hsa-miR-200b      | MIMAT0000318         |
| 5       | hsa-miR-205       | MIMAT0000266         |

TABLE X

Type 7a_sim-2 or "thirteenth sub-type-sim2" v12 miRNAs that are down regulated in normal cells and up regulated in breast and prostate tumor either grown in monolayer culture or when grown in multicellular culture.

| v12_C27 | miRNA_Type-7a-0_1 | mirbase accession no |
|---------|-------------------|----------------------|
| 1       | hsa-miR-9         | MIMAT0000441         |
| 2       | hsa-miR-9*        | MIMAT0000442         |
| 3       | hsa-miR-363       | MIMAT0000707         |
| 4       | hsa-miR-183       | MIMAT0000261         |
| 5       | hsa-miR-375       | MIMAT0000728         |
| 6       | hsa-miR-200a      | MIMAT0000682         |
| 7       | hsa-miR-429       | MIMAT0001536         |

Example 8. Evaluation of Drug Testing Platform from Tumor miRNA Profile

Figure 17:
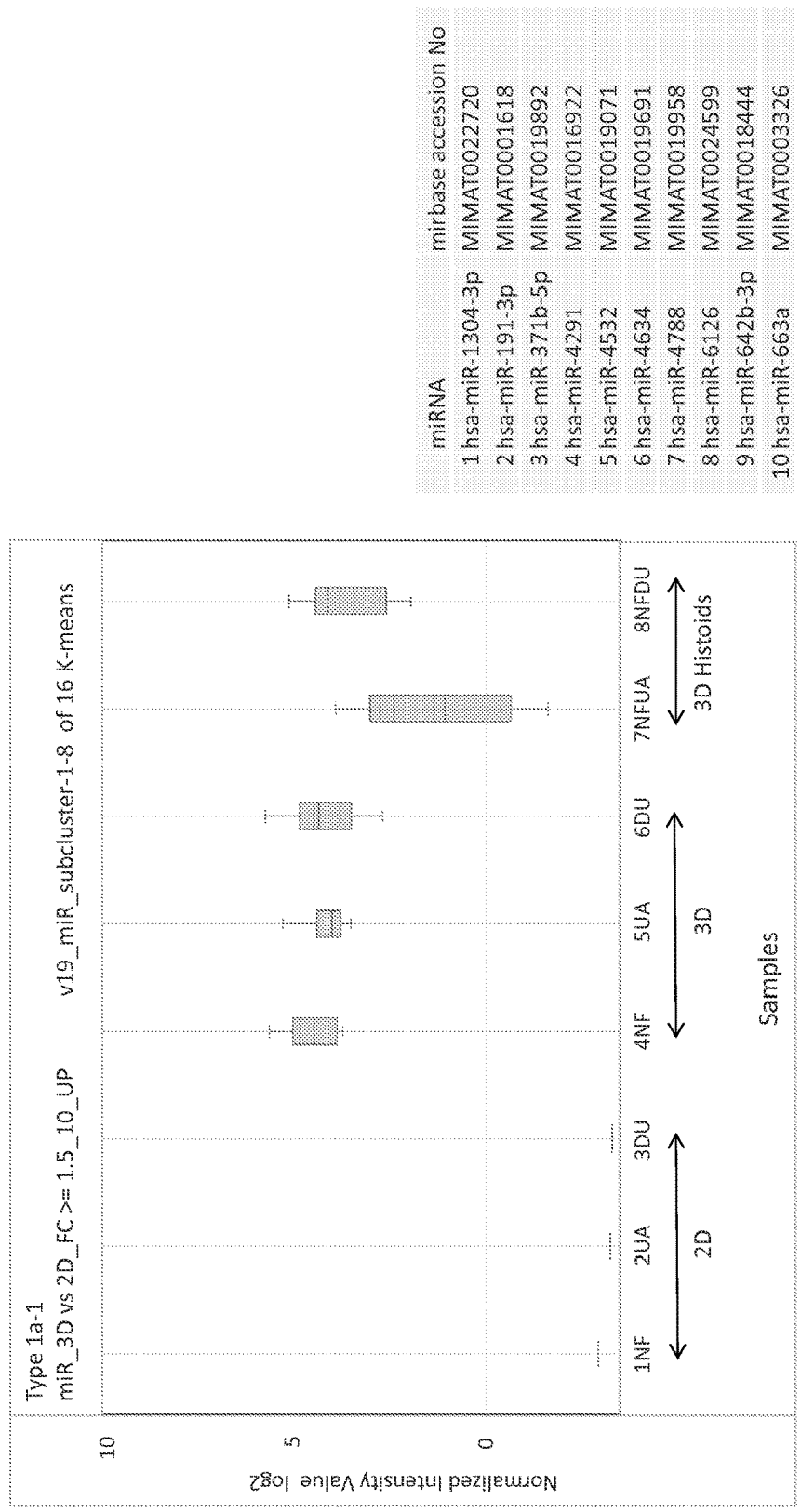
FIG. 17 shows Type 1a-1 (v19) miRNA expression pattern of 10 up regulated miRNAs in all three sample pairs of normal (NF), breast tumor (UA) and prostate tumor (DU) 3D versus 2D of sub-cluster 1-8 of 16 K-means.
Figure 18:
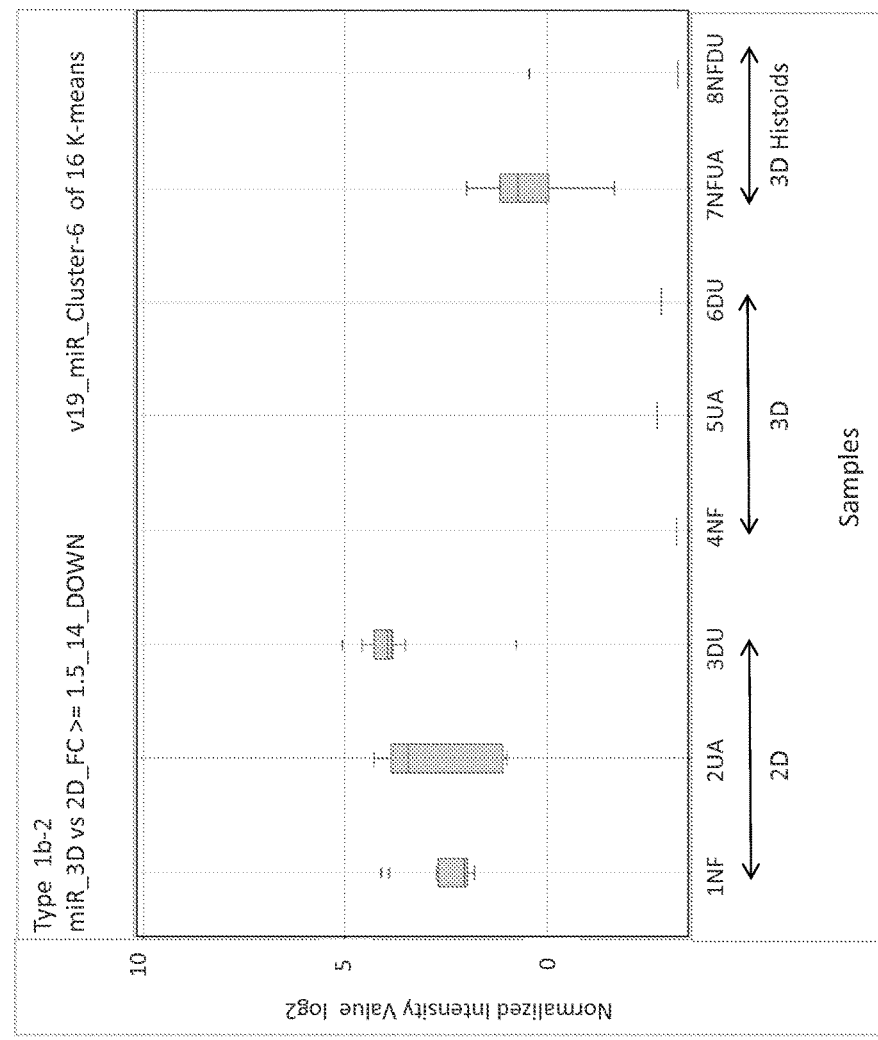
FIG. 18 shows Type 1b (v19) miRNA expression pattern of 14 down regulated miRNAs in all three sample pairs of normal (NF), breast tumor (UA) and prostate tumor (DU) 3D versus 2D of cluster 6 of 16 K-means.
Figure 19:
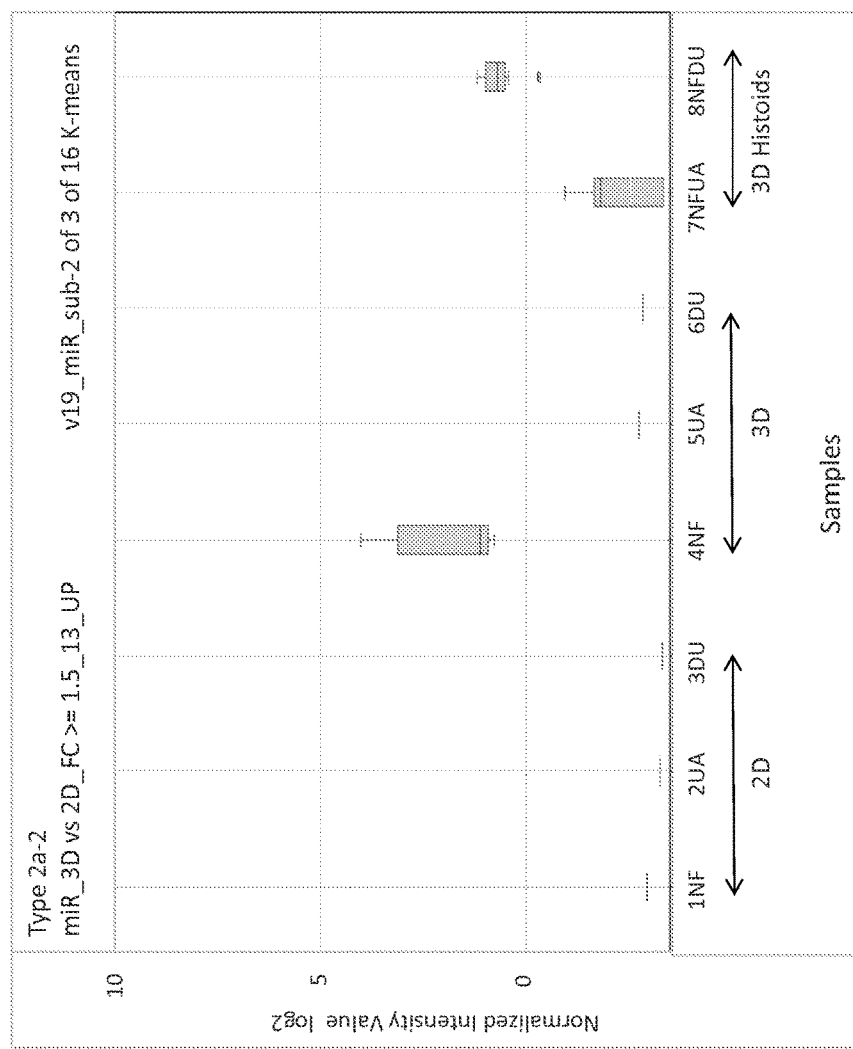
FIG. 19 shows Type 2a-2 (v19) miRNA expression pattern of 13 up regulated miRNAs in Normal 3D NF versus 2D NF of cluster 3 of 16 K-means.
Figure 20:
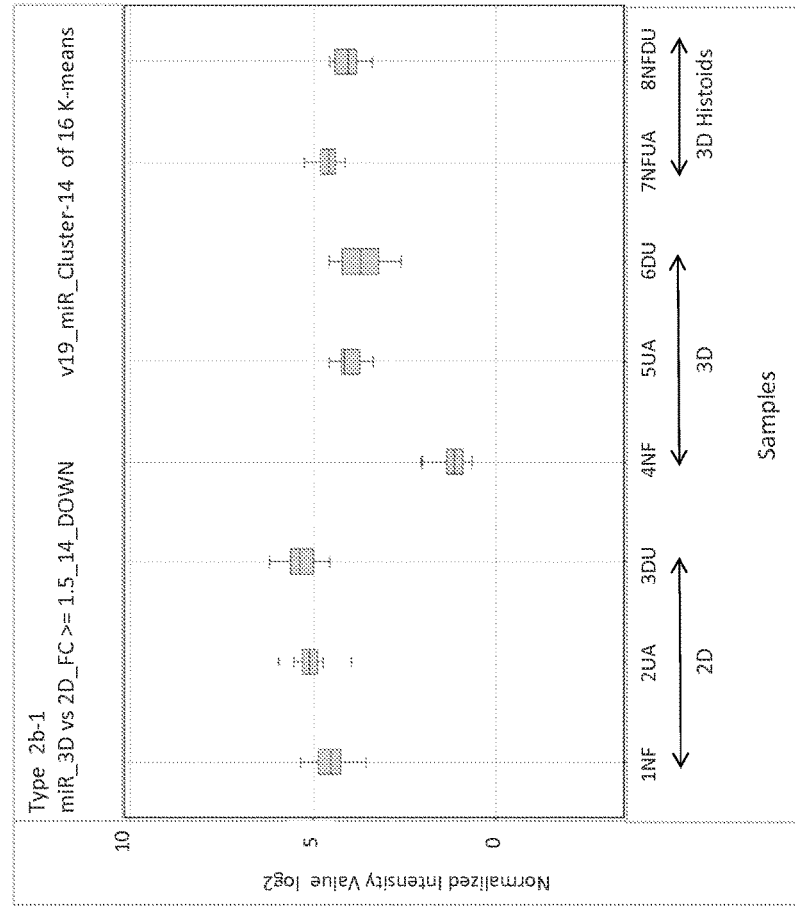
FIG. 20 shows Type 2b-1 (v19) miRNA expression pattern of 14 down regulated miRNAs in Normal 3D NF versus 2D NF of cluster 14 of 16 K-means.
Figure 21:
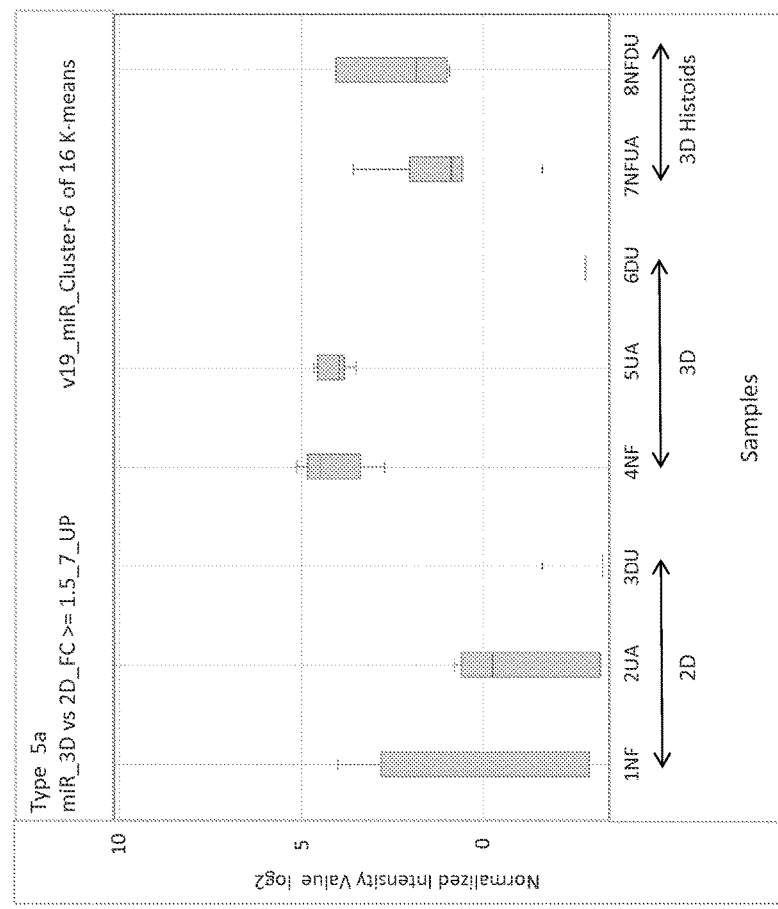
FIG. 21 shows Type 5a (v19) miRNA expression of 7 up regulated miRNAs in Normal 3D NF and breast tumor 3D UA versus 2D NF and 2D UA respectively, of cluster 6 of 16 K-means.
Figure 22:
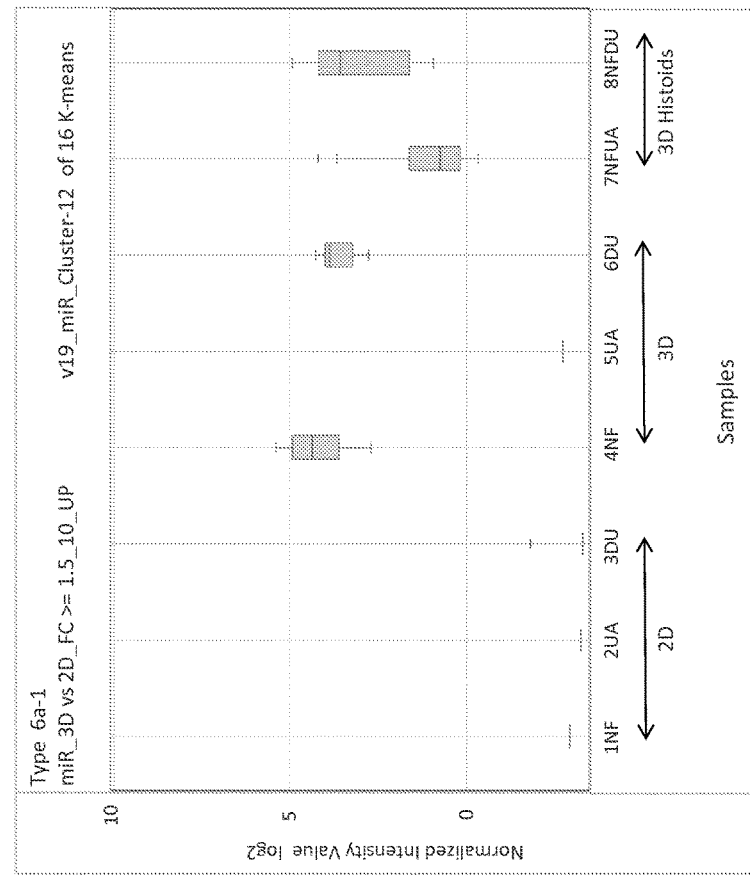
FIG. 22 shows Type 6a-1 (v19) miRNA expression of 10 up regulated miRNAs in Normal 3D NF and prostate tumor 3D DU versus 2D NF and 2D DU respectively, of cluster 12 of 16 K-means.

In the above example 7 signature miRNA for each cluster type has been identified o for informed decision making based on the molecular profile of normal and tumor cells grown in 2D monolayer and 3D multicellular culture to choose an optimal testing platform for a candidate compound to target tumor cells and tumor associated normal cells. In the above example the expression of miRNA in the cluster of Type 1a or the "first type" (Table II) in which the tumor cells whether of breast (UACC-893) or of prostate (DU-145) tumor are very similar to the normal fibroblast cells (NF) both in the 2D and 3D cultures. However, the miRNA expression levels of miRNA Type 1a-1_1 cluster (Table II and FIG. 17) shows that in 3D cultures this miRNA cluster is several fold highly expressed in 3D culture than in 2D culture. In this scenario the molecular profile information suggests that if a drug candidate that targets hsa-miRNA-371b-5p is chosen in an anti-miR therapy, then the cells grown in 3D culture should be chosen for evaluation of the chosen drug candidate since hsa-miRNA-371b-5p is undetected or not expressed in 2D culture cells. However, if the choice of the drug candidate is to target cancer cells and not normal cells then choice of the drug to target hsa-miRNA-371b-5p will target both tumor and normal cells equally. In this scenario miRNA belonging to Type 7a or the "thirteenth type" must be chosen (Table VII and FIG. 23) in which miRNA cluster is expressed in 3D of breast and prostate tumor and not in normal cells. Hence, this type of information based on molecular profile is crucial to fine tune the choice of the drug candidate compound. This example highlights as essential the importance and use of such an in-depth method for molecular characterization to type signatures of miRNA expression patterns profiles as done in this work for the choice of the culture method to be used and for a specific drug candidate to be tested and evaluated in drug development. In view of the drug attrition rates in targeted drug development such fine-tuned molecular handle with informed choice of the model and drug compound to use will help save cost in the testing, screening and treatment of oncology drugs.

The invention claimed is:

1. A method for screening a candidate molecule for possible activity against tumor cells, wherein the candidate molecule is designed to target a miRNA or a target set of miRNAs in the tumor cells, the method comprising the steps of:
   (a) obtaining or having obtained data that categorizes an array of miRNAs, including the target miRNA or target set of miRNAs, into a plurality of categories based at least in part upon a comparison of an expression profile of each miRNA in the array of miRNAs when the tumor cells and normal cells respectively are grown in a three-dimensional multicellular culture and an expression profile of each miRNA in the array of miRNAs when the tumor cells and the normal cells respectively are grown in a monolayer culture;
   (b) determining from the data whether the expression profile of the target miRNA or target set of miRNAs in the tumor cells when cultured is capable of differentiating the multicellular culture from the monolayer culture, by whether a level of expression of the target miRNA or target set of miRNAs is up regulated or down regulated and significant as a fold change of at least 1.5, when the tumor cells are grown in the multicellular culture as compared with when the tumor cells are grown in the monolayer culture;
   (c1) if the determining in step (b) shows that the expression profile of the target miRNA or set of miRNAs is capable of differentiating the multicellular culture from the monolayer culture, then performing the following steps:
      (i) growing the tumor cells in the multicellular culture;
      (ii) administering the candidate molecule to the tumor cells grown in the multicellular culture; and
      (iii) conducting an assay to look for anti-tumor activity in the multicellular culture; or
   (c2) if the determining in step (b) does not show that the expression profile of the target miRNA or set of miRNAs is capable of differentiating the multicellular culture from the monolayer culture, then performing the following steps:
      (i) growing the tumor cells in the monolayer culture;
      (ii) administering the candidate molecule to the tumor cells grown in the monolayer culture; and
      (iii) conducting an assay to look for anti-tumor activity in the monolayer culture.

2. The method of claim 1, wherein the multicellular cultures of tumor cells consist of tumor histoids.

3. The method according to claim 2, wherein the tumor histoids are prepared by (i) generating a spheroid comprising stromal cells, and (ii) culturing the generated spheroid with the malignant epithelial cells such that the malignant epithelial cells coat and invade the spheroid producing extracellular matrix during the culture and form a tumor histoid micro-tissue.

4. The method according to claim 3, wherein the candidate molecule is an anti-miRNA or a siRNA.

5. The method according to claim 1, wherein the candidate molecule is an anti-miRNA or a siRNA.

6. The method according to claim 1, wherein the data in step (a) categorizes the array of miRNAs into the following types:
   (a) a first type wherein expression of the miRNAs is down regulated or not detected when the tumor cells and normal cells are grown in monolayer culture and is up regulated and significant as a fold change of at least 1.5 when the tumor cells and normal cells are grown in multicellular culture;
   (b) a second type wherein expression of the miRNAs is up regulated when the tumor cells and normal cells are grown in monolayer cells and is down regulated and significant as a fold change of at least 1.5 when the tumor cells and the normal cells are grown in multicellular culture;
   (c) a third type wherein expression of the miRNAs is down regulated when the tumor cells and normal cells are grown in monolayer cells and is up regulated and significant as a fold change of at least 1.5 in the normal cells, but not in breast tumor cells or prostate tumor cells, when grown in multicellular culture;
   (d) a fourth type wherein expression of the miRNAs is up regulated when the tumor cells and the normal cells are grown in monolayer culture and is down regulated and significant as a fold change of at least 1.5 in the normal cells, but not breast tumor cells or prostate tumor cells, when grown in multicellular culture;

(e) a fifth type wherein expression of the miRNAs is down regulated when the tumor cells and normal cells are grown in monolayer culture and is up regulated and significant as a fold change of at least 1.5 in breast tumor cells, but not the normal cells or prostate tumor cells, when grown in multicellular culture;

(f) a sixth type wherein expression of the miRNAs is up regulated when the tumor cells and the normal cells are grown in monolayer culture and is down regulated and significant as a fold change of at least 1.5 in breast tumor cells, but not the normal cells or prostate tumor cells, when grown in multicellular culture;

(g) a seventh type wherein expression of the miRNAs is down regulated when the tumor cells and the normal cells are grown in monolayer culture and is up regulated and significant as a fold change of at least 1.5 in the prostate tumor cells, but not the normal cells or breast tumor cells, when grown in multicellular culture;

(h) an eighth type wherein expression of the miRNAs is up regulated when the tumor cells and the normal cells are grown in monolayer culture and is down regulated and significant as a fold change of at least 1.5 in prostate tumor cells, but not the normal cells or breast tumor cells, when grown in multicellular culture;

(i) a ninth type wherein expression of the miRNAs is down regulated when the tumor cells and the normal cells are grown in monolayer culture and is up regulated and significant as a fold change of at least 1.5 in the normal cells and breast tumor cells, but not prostate tumor cells, when grown in multicellular culture;

j) a tenth type wherein expression of the miRNAs is up regulated when the tumor cells and the normal cells are grown in monolayer culture and is down regulated and significant as a fold change of at least 1.5 in the normal cells and breast tumor cells, but not prostate tumor cells, when grown in multicellular culture;

(k) an eleventh type wherein expression of the miRNAs is down regulated when the tumor cells and the normal cells are grown in monolayer culture and is up regulated and significant as a fold change of at least 1.5 in the normal cells and prostate tumor cells, but not breast tumor cells, when grown in multicellular culture;

(l) a twelfth type wherein expression of the miRNAs is up regulated when the tumor cells and the normal cells are grown in monolayer cells and is down regulated and significant as a fold change of at least 1.5 in the normal cells and prostate tumor cells, but not breast tumor cells, when grown in multicellular culture;

(m) a thirteenth type wherein expression of the miRNAs is down regulated when the tumor cells and the normal cells are grown in monolayer cells and is up regulated and significant as a fold change of at least 1.5 in breast tumor cells and prostate tumor cells, but not the normal cells, when grown in multicellular culture; and (n) a fourteenth type wherein expression of the miRNA is up regulated when the tumor cells and the normal cells are grown in monolayer cells and is down regulated and the decrease is significant as a fold change of at least 1.5 in breast tumor cells and prostate tumor cells, but not the normal cells, when grown in multicellular culture.

7. The method according to claim 6, wherein the data obtained from the array of miRNAs is categorized into a plurality of types, wherein the plurality of types comprise two or more of the following types:

First type: has-miR-1304-3p,
  has-miR-191-3p,
  has-miR-371 b-5p,
  has-miR-4291,
  has-miR-4532,
  has-miR-4634,
  has-miR-4788,
  has-miR-6126,
  has-miR-642b-3p,
  has-miR-663a;
Second type: hsa-miR-103a-2-5p,
  hsa-miR-130a-5p,
  hsa-miR-1343,
  hsa-miR-15a-3p,
  hsa-miR-1913,
  hsa-miR-196b-3p,
  hsa-miR-1976,
  hsa-miR-3619-3p,
  hsa-miR-3622a-3p,
  hsa-miR-4308,
  hsa-miR-4722-3p,
  hsa-miR-4756-5p,
  hsa-miR-642b-5p,
  hsa-miR-6510-3p;
Third type: hsa-miR-129-1-3p,
  hsa-miR-1290,
  hsa-miR-146b-5p,
  hsa-miR-15b,
  hsa-miR-154-5p,
  hsa-miR-18b-3p,
  hsa-miR-19a-3p,
  hsa-miR-337-5p,
  hsa-miR-3685,
  hsa-miR-602,
  hsa-miR-625-3p,
  hsa-miR-6722-3p,
  hsa-miR-98-3p;
Fourth type: hsa-let-7d-3p,
  hsa-miR-1255b-2-3p,
  hsa-miR-300,
  hsa-miR-33a-3p,
  hsa-miR-3927-5p,
  hsa-miR-4474-5p,
  hsa-miR-4493,
  hsa-miR-5088,
  hsa-miR-5090,
  hsa-miR-539-5p,
  hsa-miR-609,
  hsa-miR-640,
  hsa-miR-6500-5p,
  hsa-miR-765;
Ninth type: hsa-miR-1227-5p,
  hsa-miR-125a-3p,
  hsa-miR-132-3p,
  hsa-miR-196a-5p,
  hsa-miR-572,
  hsa-miR-99a-5p,
  hsa-miR-99b-5p;
Eleventh type: hsa-miR-2116-3p,
  hsa-miR-30e-5p,
  hsa-miR-31-3p,
  hsa-miR-3676-3p,
  hsa-miR-4270,
  hsa-miR-4310,
  hsa-miR-4731-3p, hsa-miR-4745-5p,
hsa-miR-5195-3p,
hsa-miR-6723-5p; and Thirteenth type: hsa-miR-18 3-5p,
hsa-miR-378a-3p,
hsa-miR-4 299,
hsa-miR-96-5p.

8. The method according to claim 3, wherein the malignant epithelial cells are malignant breast, prostate, colon, pancreas or urinary bladder cells.

9. The method according to claim 8, wherein the malignant epithelial cells are malignant breast or prostate cells.

10. The method according to claim 9, wherein the stromal cells are fibroblast cells.

11. The method according to claim 10, wherein the tumor histoid culture is prepared by a low shear, rotating suspension culture.

12. The method according to claim 10, wherein the tumor histoid culture model is prepared using hanging drop culture plates to provide a high throughput screening.

13. The method according to claim 1, further comprising searching a miRNA gene target database to correlate the target miRNA or target set of miRNAs with a mRNA target of known function to ascertain a role of the at least one miRNA in a gene expression network, wherein the gene interaction network is for cellular processes selected from the group consisting of (i) epigenetics; (ii) inflammation; (iii) apoptosis and (iii) angiogenesis.

14. The method according to claim 13, wherein the gene interaction network is an epigenetic cellular process for chromatin architecture modification and target set of miRNAs comprises hsa-miR-455-3p, hsa-miR-224, hsa-miR-132, hsa-miR-99a, and hsa-miR-196b.

15. The method according to claim 13, wherein the gene interaction network is an inflammation cellular process and the target set of miRNAs comprises hsa-miR-146b-5p, hsa-miR-188-5p, hsa-miR-134, hsa-miR-1290, hsa-miR-1246, and hsa-miR-630.

16. The method according to claim 13, wherein the gene interaction network is a cellular process for apoptosis and the target set of miRNAs comprises hsa-miR-155, hsa-miR-136, hsa-miR-299-5p, hsa-miR-381, and hsa-miR-487b.

17. The method according to claim 13, wherein the gene interaction network is an angiogenesis cellular process for blood vessel formation and the target set of miRNAs comprises hsa-miR-141, hsa-miR-96, hsa-miR-200c, hsa-miR-200b, hsa-miR-205 and miRNA sub-cluster hsa-miR-9, hsa-miR-9*, hsa-miR-363, hsa-miR-183, hsa-miR-375, hsa-miR-200a and hsa-miR-429.

18. The method according to claim 1, wherein the target miRNA or set of miRNAs are evaluated in a sample tissue of a solid tumor in a patient's breast or prostate.

19. The method according to claim 1, wherein the data in step (a) has been obtained by a bioinformatics analysis that categorizes the array of miRNAs into a plurality of types by:
  (a) comparing respective levels of expression of the miRNAs in each of the following groups: (i) normal cells cultured in the monolayer culture as compared with the multicellular culture; (ii) a first type of tumor cells cultured in the monolayer culture as compared with the multicellular culture; and (iii) a second type of tumor cells cultured in the monolayer culture as compared with the multicellular culture, and
  (b) based on the comparing, categorizing the array of miRNAs such that the plurality of types comprises miRNAs whose expression profiles are (i) unique to the first type of tumor cells, (ii) unique to the second type of tumor cells; and (iii) common to both the first and second types of tumor cells.

* * * * *